US006451765B1

(12) United States Patent
Ervin, Jr.

(10) Patent No.: US 6,451,765 B1
(45) Date of Patent: Sep. 17, 2002

(54) METHODS FOR TREATING BREAST CANCER USING MAMMASTATIN

(75) Inventor: Paul R. Ervin, Jr., Ann Arbor, MI (US)

(73) Assignee: University of Michigan, Ann Arbor, MI (US)

( * ) Notice: Subject to any disclaimer, the term of this patent is extended or adjusted under 35 U.S.C. 154(b) by 0 days.

(21) Appl. No.: 09/285,379

(22) Filed: Apr. 2, 1999

Related U.S. Application Data

(62) Division of application No. 08/943,828, filed on Oct. 3, 1997, now abandoned.
(60) Provisional application No. 60/027,315, filed on Oct. 3, 1996.

(51) Int. Cl.$^7$ .......................... A01N 37/18; A61K 38/00; A61K 39/00; G01N 33/48

(52) U.S. Cl. ................................ 514/21; 514/2; 514/7; 424/184.1; 424/198.1; 436/64

(58) Field of Search ................. 514/2, 7, 21; 424/184.1, 424/198.1; 436/64

(56) References Cited

U.S. PATENT DOCUMENTS

| | | |
|---|---|---|
| 4,379,839 A | 4/1983 | Spiegelman |
| 4,753,894 A | 6/1988 | Frankel et al. |

OTHER PUBLICATIONS

Blat, C. et al., (Jul. 1986) *Fed. of Europe. Biochem. Soc.*, 203(2):175–180 "Inhibitor Diffusible Factor IDF45, A G1 Phase Inhibitor".
Bohmer et al., (1985) *Biochem. Biophys. Acta.*, 846:145–154 "Specific Neutralizing Antiserum Against a Polypeptide Growth Inhibitor for Mammary Cells Purified from Bovine Mammary Gland".
Bohmer, F.D. et al., (1984) *Experimental Cell Research.*, 150:466–476 "Purification of a Growth Inhibitor for Ehrlich Ascites Mammary Carcinoma Cell from Bovine Mammary Gland".
Bohmer, F.D. et al., (Nov. 5, 1987) *J. Biol. Chem.*, 262(31):15137–15143 "Identification of a Polypeptide Growth Inhibitor from Bovine Mammary Gland".
Bronzert, D. et al., (Mar. 1987) *Cancer Research.*, 47: 1234–1238 "Estrogen Inhibitor of a M, 39,000 Glycoprotein Secreted by Human Breast Cancer Cells".
Budzic, G.P. et al., (1985) *Devel. Mech.: Normal and Abnormal*, 207–223, Alan R. Liss, Inc. "A Possible Purification of Mullerian Inhibitingy Substance and a Model for its Mechanism of Action".
Burgess, A.W. et al., (1976) *J. Cell. Physiol.*, 90:471–484 "The Effect of Colony Stimulating Factor on the Synthesis of Ribonucleic Acid by Mouse Bone Marrow Cells in Vitro".

Dalchau et al., (1982) *Monoclonal Antibodies in Clinical Medicine*, pp. 519–552 "The Purification of Antigens and other Studies with Monoclonal Antibody Affinity Columns: the Complementary New Dimension of Monoclonal Antibodies".
Database Dissertation Abstracts Session No. AA19542835 (1995).
Dell' Aquila, et al., (1984) *Journal of the National Cancer Institute*, 72:291–298 "A Factor from Plasma–Derived Human Serum that Inhibits the Growth of the Mammary Cell Line MCF–7: Characterization and Purification".
Dell' Aquila, et al., (Dec. 1984) *Dissertation Abs. International*, 45(6):1649B–1650B "Characterization and Purification of a Factor from Plasma Derived Human Serum which Inhibits the Growth of the Mammary Cell Line MCF–7".
Dickson, R.B. et al., (Feb. 1987) *PNAS USA*, 84:837–841 "Activation of Growth Factor Secretion in Tumorigenic States of Breast Cancer Induced by 17–beta–estradiol or v–Ha–ras Oncogene".
Ervin et al., (1988) *Proceedings of AACR*, 29(230):58 "A 40KD Autocrine Growth Inhibitor Produced by Human Mammary Cells".
Goding, JW (1983) Monoclonal Antibodies: Principles and Practice, *Academic Press*, New York, pp. 56–97.
Goding, JW (1983) Monoclonal Antibodies: Principles and Practices, *Academic Press*, New York, pp. 250–261.
Holley, R. W. et al., (Oct. 1980) *PNAS USA*, 77(10):5989–5992 "Purification of Kidney Epithelial Cell Growth Inhibitors".
Hsu, Y. et al., (Apr. 1984) *PNAS USA*, 81:2107–2111 "Growth Control in Cultured 3T3 Fibroblast: Neutralization and Identification of a Growth–Inhibitory Factor by a Monoclonal Antibody".
Hsu, Y. et al., (Feb. 1986) *J. Cell. Biol.*, 102:362–369 "Growth Control in Cultured 3T3 Fibroblasts. V. Purification of an M, 13,000 Polypeptide Responsible for Growth Inhibitory Activity".
Huff, K.K. et al., (Sep. 1986) *Cancer Research*, 46:4613–4619 "Secretion of an Insulin–like Growth Factor-I–related Protein by Human Breast Cancer Cells".
Hunter, T., (Jul. 1986) *Nature*, 322:14–16 "Cell Growth Control Mechanisms".

(List continued on next page.)

*Primary Examiner*—Susan Ungar
*Assistant Examiner*—Gary B. Nickol
(74) *Attorney, Agent, or Firm*—Merchant & Gould P.C.

(57) ABSTRACT

A nucleic acid sequence encoding Mammastatin, a specific mammary cell growth inhibitor. Mammastatin is encoded by a single nucleic acid sequence and has an approximate molecular weight of 44 kDa in its inactive, non-phosphorylated form. Normal mammary cells express functional phosphorylated forms having approximate molecular weights of 53 kDa and 49 kDa. Metastatic mammary cells either do not express Mammastatin at all, or do not express the 53 kDa or 49 kDa, phosphorylated forms. Mammary cancer cells are inhibited in their growth by the administration of phosphorylated Mammastatin.

18 Claims, 18 Drawing Sheets

OTHER PUBLICATIONS

Kasukabe, T. et al., (Apr. 1988) *J. Biol. Chem.*, 263(11):5431–5435 "Purification of a Novel Growth Inhibitory Factor for Partially Differentiated Myeloid Leukemic Cells".

Kohler et al., (1975) *Nature*, 256:495–497 "Continous Cultures of Fused Cells Secreting Antibody of Predefined Specificity".

Lippman, M.E. et al., (1986) *Breast Cancer Res. Treat.*, 7:59–70 "Autocrine and Paracrine Growth Regulation of Human Breast Cancer".

Marx, J.L., (May 1986) *Res. News*, 30:1093–1095 "The Yin and Yang of Cell Growth Control".

McGrath et al., (1984) *In Vitro*, 20:652–662 "Calcium Regulation of Normal Human Mammary Epithelial Cell Growth in Culture".

McMabon, J.B. et al., (Feb. 1984) *J. Biol. Chem.*, 259(3):1803–1806 "Distribution and Subcellular Localization of a Hepatic Proliferation Inhibitor in Rat Liver".

Nicola, N.A. et al., (1985) *Cancer Surveys*, 4(4):789–811 "The Colony–Stimulating Factors and Myeloid Leukaemia".

Pigott et al., (1978) *In Vitro*, 14:360 "Inhibition of Growth of a Human Mammary Cell Line by Normal Human Serum".

Sachs, L., (Jan. 1986) *Scientific American*, pp. 40–47 "Growth, Differentiation and the Reversal of Malignancy".

Saxon, P.J. et al., (Jan. 1985) *Mol. Cell. Biol.*, 5(1):140–146 "Selective Transfer of Individual Human Chromosomes to Recipient Cells".

Soto, A.M. et al., (Aug. 1984) *Biochem. Biophys. Res. Comm.*, 122(3):1097–1103 "Mechanism of Estrogen Action on Cellular Proliferation: Evidence for Indirect and Negative Control on Cloned Breast Tumor Cells".

Soto, A.M., et al., (May 1986) *Cancer Res.*, 46:2271–2275 "Control of Cell Proliferation: Evidence for Negative Control on Estrogen–Sensitive T47D Human Breast Cancer Cells".

Sporn, M.B. et al., (Sep. 1987) *J. Cell Biology*, 105:1039–1045 "Some Recent Advances in the Chemistry and Biology of Transforming Growth Factor–Beta".

Tucker, R.F., et al., (Nov. 1984) *Science*, 226:705–707 "Growth Inhibitor from BSC–1 Cells Closely Related to Platelet Type–beta Transforming Growth Factor".

U.S. application No. 07/355,963, CA 2017236 laid open date: Nov. 22, 1990, but not granted.

Ervin, P.R. et al, (1995) *Proceedings of the American Association for Cancer Research, Annual Meeting*, 36:627, Abstract #3731, "The Active Species of Mammastatin as Expressed in Normal Mammary Cells but not in Mammary Carcinomas".

Ervin, P.R., (Mar. 1996) *Proceedings of the American Association for Cancer Research Annual Meeting*, 37:399, Abstract #2722, "Expression and Testing of Recombinant Mammastatin".

Ervin, P.R. et al., (1993) *Proceedings of the American Association for Cancer Research, Annual Meeting*, 34:150, Abstract #893, "Phosphoralation of the Growth Inhibitor Mammastatin in Normal but not Transformed Human Mammary Cells".

Ervin, P.R. et al., (Jun. 30, 1989) *Science*, 244:1585–1587 "Production of Mammastatin, a Tissue Specific Growth Inhibitor by Normal Human Mammary Cells".

Ervin, P.R., (1995) PHD Thesis from the University of Michigan, pp. 1–131 "Further Characterization and Cloning of the Growth Inhibitor Mammastatin".

Freemont et al., (Jan. 1984) *Archives of Biochemistry and Biophysics*, 228(1):342–352 "Human Skeletal–Muscle Aldolase: N–Terminal Sequence Analysis of CNBr–and o–Iodosobenzoic Acid–Cleavage Fragments".

Garner, I., (1994) *Methods of Molecular Biology*, 28:41–47 "Isolation of Total and Poly A+ RNA from Animal Cells".

Jerala, (1992) *Biotechniques*, 13:564 "Simultaneous Synthesis of Degenerate Oligo–nucleotides of Variable Length".

Kroczek, R.A., (1993) *Journal of Chromatography*, 618:133–145 "Review: Southern and Northern analysis".

Lasken, R.S. et al., (1985) *Proceedings of the National Academy of Science U.S.A.*, 82(5):1301–1305 "A fidelity assay using "dideoxy" DNA sequencing: A measurement of sequence dependence and frequency of forming 5–bromouracil guanine base mispairs".

Nakayama, K. et al., (Jun. 1988) *Bio/Technology*, 6:693–697 "Construction of an ASD+ Expression–Cloning Vector: Stable Maintenance and High Level Expression of Cloned Genes in a Salmonella Vaccine Strain".

Nguyen, B. et al., (1995) *Critical Reviews and Oncology/Hematology*, 20:223–236 "The Biology of Growth Regulation in Normal and Malignant Breast Epithelium: From Bench to Clinic".

Short, J.M. et al., (Aug. 11, 1988) *Nucleic Acids Research*, 16(15):7583–7601 "λ Zap: a bacteriophage λ expression vector with in vivo excision properties".

Soule, et al., (Jan. 1986) *In Vitro Cellular & Developmental Biology*, 22(1):6–12 "A Simplified Method For Passage and Long–Term Growth of Human Mammary Epithelial Cells".

Stuckey, J.A. et al., (Aug. 18, 1994) *Nature*, 370:571–575 "Crystal structure of Yersinia protein tyrosine phosphatase at 2.5 Å and the complex with tungstate".

Towbin H. et al., (1989) *Journal of Clinical Chemistry, Clinical Biochemistry*, 27(8):495–501 "Immunoblotting in the Clinical Laboratory".

Ullah et al., (Aug. 30, 1994) *Biochemical and Biophysical Research Communications*, 203(1):182–189 "The Complete Primary Structure Elucidation of *Aspergillus Ficuum* (NIGER), pH 6.0, Optimum Acid Phosphatase".

Ervin et al., Proc. Amer. Assoc. For Cancer Res. vol. 37, p. 399, Apr. 2, 1996.

METHODS FOR TREATING BREAST CANCER USING MAMMASTATIN

This application is a Divisional of Ser. No. 08/943,828, filed Oct. 3, 1997, now abandoned, which claims the benefit of priority of U.S. Provisional Patent Application Serial No. 60/027,315, filed Oct. 3, 1996, now abandoned, all of which are hereby incorporated in their entirety.

BACKGROUND OF THE INVENTION

Breast cancer is a disease that kills over 45,000 women each year in the United States alone. Over 180,000 new cases of breast cancer are diagnosed annually, and it is estimated that one in eight women will develop breast cancer. These numbers indicate that breast cancer is one of the most dangerous diseases facing women today. Cancer research has been unable to determine the cause of breast cancer, and has not found a suitable method of therapy or prevention.

A woman diagnosed with breast cancer may be treated with surgery, hormone therapy, chemotherapy, and radiation. If the patient develops metastatic disease, radiation and high dose chemotherapy are required to ablate the cancer in remote areas such as the brain, bone, and liver.

The current therapies available for the treatment of breast cancer are toxic, dangerous, costly, and many are ineffective, especially in the treatment of metastatic disease. The table below was extracted from Churchill Livingston, *Clinical Oncology*, 1995, and summarizes data available on the current methods of treatment and expected survival rates.

treatment after surgical removal of tumors. Other applications include a growth inhibitor as a primary therapy and for preventative use.

Detection methods for breast cancer, such as mammogram, physical exam, CAT-scan, and ultrasound, have significantly improved early detection of breast cancer. However, with these methods, a suspected tumor must still be surgically removed for pathological examination to determine if the tumor is benign or malignant, and to attempt to determine the tissue type and grade of the malignancy. This pathological diagnosis helps to determine what subsequent treatment protocols may be used.

For breast cancer, these methods are generally inconclusive, as adequate breast cancer tumor markers are not available. Available markers such as CA 15-3 and CA 27-29 are used as indicators of metastases, however, they are not specific. There is a great need for diagnostic tools and methods that can effectively and reliably diagnose breast cancer, e.g., using new and specific breast cancer markers. In addition, a reliable and simple method for the early detection and diagnosis of breast cancer is greatly needed. Preferably, such an early detection method would identify breast cancer in its early stages, track progression of breast cancer through advanced metastatic disease, and diagnose the propensity of a patient to develop breast cancer or to develop advanced disease. Most preferably, the diagnostic method could be used without tissue biopsy, e.g., by analysis of a body fluid such as blood.

Human mammary tissues undergo a burst of proliferative activities at the onset of menarche and during each menstrual cycle. Studies on the effects of estrogen on mammary

| Treatment | Method | Effect | Toxicity | Result | Survival |
|---|---|---|---|---|---|
| adriamycin | bolus | kill cancer cells | high | can induce remission | +14 months |
| cyclophosphate | bolus | kill cancer cells | high | can induce remission | +16 months |
| methotrexate | infusion | kill cancer cells | high | can induce remission | +16 months |
| 5F uracil | infusion | kill cancer cells | high | can induce remission | +18 months |
| mix of above | mixed | kill cancer cells | high | can induce remission | +22 months |
| taxol | bolus | kill cancer cells | high | can induce remission | +12 months |
| estrogen | oral | may stop growth | low | can induce remission | +6 months |
| tamoxifen | oral | may stop growth | low | may stop progression | +12 months |
| mastectomy | surgery | remove tumor | low | may eliminate cancer | +5 years* |
| lumpectomy | surgery | remove tumor | low | may eliminate cancer | +5 years* |
| surgery and tamoxifen | combination | combination | low | may eliminate cancer | +7–10 years* |
| radiation | mechanical | kill cancer cells | high | can induce remission | +14 months |

*assumes there are no micrometasteses

Currently, there are no therapies that are effective for long term treatment of breast cancer that has metastasized to lymph nodes or distal sites. Local disease can be effectively treated by surgery, if all of the cancer can be removed. A new therapy for the effective treatment of breast cancer that could stop the growth of breast cancer and of cells derived from metastatic cancer is urgently needed. Such a therapy would be useful in the treatment of localized breast cancer, in long term treatment of metastatic disease, and as a follow-up tissues and tumors indicate that estrogen is a primary growth-initiating factor for mammary tissues. Estradiol-sensitive growth factors have been characterized. In addition, mammary cell growth factors which are not hormonal in nature have also been described.

Specific growth factors which have been shown to have a stimulating effect on mammary tissue growth include platelet-derived growth factor (PDGF), insulin-like growth factor (IGF-1) and transforming growth factor (TGF) alpha.

TGF-beta, on the other hand, has been shown to suppress mammary tissue growth.

The regulation of mammary cell growth is of great importance in the diagnosis and treatment of breast cancer. Neoplastic growth of mammary tissues, if unchecked, can develop into uncontrollably-proliferating malignant tumors, which are the cause of death of thousands of women yearly. A growth inhibition factor capable of specifically suppressing mammary cell growth would provide a dynamic tool for use in the diagnosis and treatment of breast cancer.

Thus, it would be of great utility to isolate and characterize a specific mammary cell growth inhibitor, to identify its nucleic acid sequence and amino acid sequence, and to recombinantly express the inhibitor as a purified protein. Diagnostic and therapeutic methods using the nucleic acid sequence and/or recombinantly produced inhibitor would be of great utility in the diagnosis and treatment of breast cancer.

SUMMARY OF THE INVENTION

A specific mammary cell growth inhibitor, Mammastatin, has been isolated from normal human mammary cells and characterized. It has now been found that Mammastatin is produced by normal mammary cells, but not by breast cancer cells. Furthermore, it has now been found that the reduction or absence of Marunastatin in the blood correlate with the presence of breast cancer. Administration of active Mammastatin prevents growth of breast cancer cells.

The nucleic acid sequence encoding Mammastatin has now been cloned, sequenced, and expressed recombinantly in host cells as an active inhibitor of mammary cell growth. The isolated and characterized nucleic acid sequence (Sequence ID No: 1) and its deduced amino acid sequence provide unique and specific tools for use in the diagnosis and treatment of breast cancer.

The present invention provides an isolated and purified nucleic acid sequence encoding Mammastatin, a specific protein inhibitor of mammary cell growth, and particularly of mammary cancer cell growth. The invention also includes plasmids and vectors containing the Mammastatin nucleic acid sequence, amino acid sequence of Mammastatin, and methods, kits, and compositions utilizing the Mammastatin nucleic acid or amino acid sequences to produce purified mammary cell growth inhibitor and in the diagnosis and treatment of breast cancer. The inventive compositions include probes and primers that specifically hybridize to the Mammastatin nucleic acid sequence and its RNA products.

The invention further includes a method for treating breast cancer by administering Mammastatin.

DETAILED DESCRIPTION OF THE PREFERRED EMBODIMENTS

Mammastatin

Figure 1:
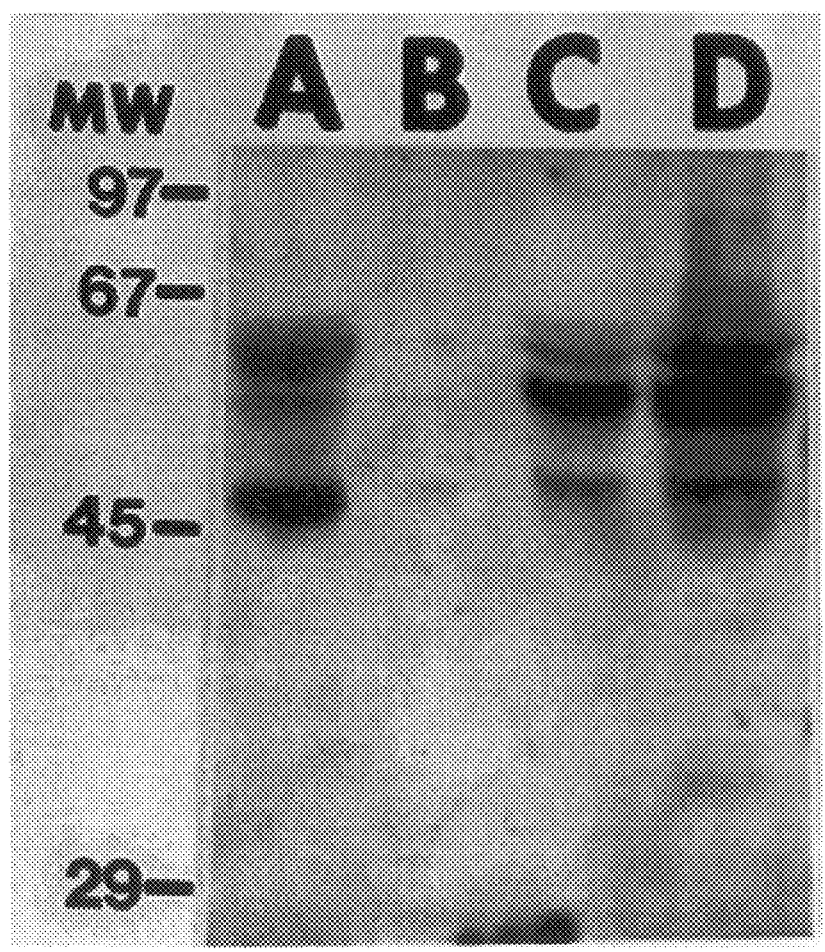
FIG. 1 is a Western Blot showing expression of recombinant Mammastatin in Eucaryotic Cos-7 cells.

Mammastatin is a protein growth inhibitor produced and secreted by normal human mammary epithelial cells. A mammary cell growth inhibitor was first described as an inhibitory protein activity present in media conditioned by the growth of normal human mammary cells. The inhibitory activity was identified in conditioned medium from normal human mammary cells, but not in media conditioned by the growth of human mammary cancer cells. The inhibitory activity was determined by bioassay and antibody development to reside in three proteins, having the approximate molecular weights of 53, 49 and 44 kDa (Ervin, Paul R., Doctoral Dissertation University of Michigan, 1995).

It has now been determined that a specific mammary cell growth inhibitor, Mammastatin, is expressed as a 44 kD protein which is phosphorylately increasing the molecular weight to 49 kD and 53 kD. The non-ph 44 kD form is not an active inhibitor, whereas the Phosphorylated 49 kD and 53 kD forms inhibit growth of breast cancer cells. The active 53 and/or 49 kD phosphoprotein is expressed by normal human mammary cells, but is not generally produced by human mammary carcinoma cells. Some carcinoma cells make the 44 kD protein that lacks phosphorylation and is inactive.

The table below summarizes data showing expression and activity of Mammastatin in normal and cancerous cells and tissues.

| Cell Type* | Number | 44 kDa** | 53/49 kDa** | produce inhibitor | are inhibited |
|---|---|---|---|---|---|
| Normal primary cultures | 42 | +/− | ++++ | 42/42 | 2/2 |
| Normal breast tissue | 5 | + | ++ | | |
| Mammary Cell Line | 16 | | | 0/16 | 12/12 |
| Type A | 11 | + | − | 0/11 | 8/8 |
| Type B | 5 | − | − | 0/5 | 4/4 |
| Breast tumor lysate | 25 | | | | |
| Type A | 17 | + | − | | |
| Type B | 8 | − | − | | |
| Non-mammary cell lines | 8 | | | 0/2 | 0/8 |
| Type A | 3 | + | −*** | 0/1 | 0/3 |
| Type B | 5 | − | −*** | 0/1 | 0/5 |

*Carcinoma cells in which 44 kDa Mammastatin was detected (Type A) or not (Type B)
**(−) No expression
(++++) intense expression
***Two cell lines, BxPc3 and A253 expressed proteins identified as 53/49 kD, but neither cell line produced inhibitory activity.

Dose response studies with human mammary carcinoma cells indicates that carcinoma cell growth is 50–70% inhibited with 10 ng/ml of Mammastatin and blocked completely with 25–50 ng/ml. Highly metastatic cells such as MDA-MB-435 and MDA-MB-231 required 50 ng/ml to stop growth. In vitro and in vivo clinical data experiments indicate the effect is reversible, and that repeated administration of the inhibitor is required to arrest carcinoma cell growth at the lower concentrations. At doses above 50 ng/ml, however, Mammastatin appears to induce apoptosis, as indicated by histology, e.g. cell necrosis.

Since Mammastatin is a natural growth inhibitor that blocks mammary carcinoma cell growth, and since no tumors make active Mammastatin, Mammastatin replacement therapy is ideal for therapeutic treatment of breast cancer. The clinical data provided in the examples below demonstrate the effectiveness of Mammastatin replacement therapy.

The nucleic acid sequence encoding Mammastatin protein has now been isolated, characterized, sequenced (Sequence ID NO:1), determined to encode all three (53, 49, and 44 kD) molecular weight proteins, and given the name "Mammastatin". Differences in the molecular weight of the three forms has been determined to be caused by the extent of the protein's phosphorylation. Mammastatin produced by normal human mammary cells (NHMC) in culture and recombinantly expressed Mammastatin inhibit the growth of human mammary carcinoma cells, and is useful as a therapeutic agent in the treatment of breast cancer.

Analysis of human sera from normal women and from breast cancer patients indicates that decreased blood levels of Mammastatin correlate with advancing breast cancer. Screening and monitoring blood serum for the presence of this active inhibitor as described in the examples below provides a specific and effective diagnostic tool.

Nucleic Acid Sequence

The Mammastatin DNA nucleic acid (SEQ ID NO:1) is shown in Table 1 below, and was identified by cloning and sequencing of Mammastatin cDNA from a normal human mammary cell cDNA library, as described more fully in the Examples below. Chromatographically purified inhibitor had not previously been sufficiently isolated to permit its amino acid analysis, and early attempts to sequence the protein inhibitor by standard techniques failed. Attempts to screen a cDNA library using antibodies raised against chromatographically purified inhibitor protein failed to generate an active clone. To overcome these problems, the gene encoding Mammastatin was identified by peptide sequencing and degenerate oligonucleotide screening of a normal human mammary cell cDNA library.

Concentrated protein produced by normal human mammary cells was affinity purified using an anti-Mammastatin antibody raised against chromatographically purified inhibitor. Purified protein fractions were supplemented with a small amount ($10^5$ cpm) of $^{32}P$ labeled as tracers. The labeled tracer protein was purified from conditioned media of cells grown in the presence of $^{32}P$, as described more fully in the examples below. The protein was cleaved with Cyanogen bromide, and cleaved fragments were identified as Mammastatin by autoradiographic analysis of $^{32}P$-labeled protein. The most abundant labeled peptides generated by the cleavage were sequenced.

Two peptides, selected as having unique amino acid sequences (seq. ID Nos. 2 and 3), were used to produce degenerate oligonucleotides. The degenerate oligonucleotides were then used to screen a normal human mammary cell cDNA library.

One clone, labeled pMammA, hybridized to oligonucleotides from both selected peptides. This clone was further characterized, and was shown to express protein recognized by anti-Mammastatin antibodies. The clone has been verified as encoding Mammastatin by Northern blot analysis, in vitro transcription and translation assays, and growth inhibition assays. A pcDNA3 clone containing the Mammastatin cDNA insert (pMammB) was deposited with the American Type Culture Collection and given Accession Number 97451. The recombinant protein expressed from pMammnB has been detected by immunoblot of transfected mammalian cell lines and has been demonstrated to possess growth inhibitory activities against mammary cancer cells. The cDNA clone has been completely sequenced (see Example 3) and found to be unique to the BLAST DNA database.

The nucleic acid sequence of the invention (Sequence ID No: 1) encodes human Mammastatin, which functions to inhibit the growth of human mammary cells, normal and cancerous. The term "human" is not intended to limit the source of the protein nor to limit its inhibitory effects only to human cells and tissues. It is understood that the nucleic acid sequence and amino acid sequence of Mammastatin in individuals may vary somewhat, without altering the structure or function of the protein. Further, one skilled in biochemistry will appreciate that modifications of the nucleic acid or amino acid sequence may be made without altering the structure and/or function of the molecule. For example, the nucleic acid sequence may be modified to permit optimal expression of the desired amino acid sequence using known optimal codons for a particular cellular host.

The nucleic acid sequence of the invention is useful in producing large quantities of highly purified Mammastatin protein for use in therapeutic and diagnostic methods in the treatment of breast cancer.

Anti-Mammastatin Antibodies

Several anti-Mammastatin antibodies have been produced and characterized. See, for example, PCT application WO 89/11491 published Nov. 30, 1989. These antibodies were raised against chromatographically purified inhibitor protein, and have been demonstrated to block the inhibitory effect of Manimastatin protein on mammary cell growth.

Available anti-Mammastatin antibodies include 7G6 and 3C6, commercially available from Neomarkers (Freemont, Calif.) and 6B8. Hybridoma cells producing 6B8 antibody are available from the American Type Culture Collection (ATCC No. HB 10152). Each of these antibodies binds to all three molecular weight forms of Mammastatin and are useful in immunological assays, including dot blots and Western blots. The 7G6 antibody is preferred for Western blot analysis or for ELISA analysis of denatured protein samples. The antibodies 3G6 and 6B8 may be used in ELISA assays, e.g., under conditions specified in the examples.

Additional antibodies can be produced using standard methods known for producing monoclonal or polyclonal antibodies. The antigen used to produce antibodies may be derived from culture of NHMC or from recombinantly expressed Mammastatin.

Diagnostic Method

The invention further provides an in vitro assay for detecting active, inhibitory Mammastatin in patient samples, including tissues, cells, and fluids. Breast cancer disease and advancing metastatic disease is diagnosed by correlating the presence and type of Mammastatin protein in a patient's sample with that of normal or cancerous human mammary cells. A patient's blood or tissue sample is analyzed for mammastatin protein, e.g., for the abundance of Mammastatin protein and/or for the molecular weight forms of Mammastatin. As discussed below, the absence or loss of Mammastatin, particularly of the higher molecular weight, phosphorylated forms of Mammastatin, is correlated with breast cancer and indicative of advancing metastatic disease.

Analysis of Mammastatin is preferably by immunoassay, including ELISA or Western Blot analysis of a patient's blood samples, using anti-Mammastatin antibodies. Preferably, recombinant Mammastatin standards are used to provide a standard curve for reliable quantitation of inhibitor levels. Such immunoassays are exemplified by the dot-blot assays and Western blot assays shown in the examples below. In an alternative preferred embodiment of the invention, tissue samples, such as tumor biopsies, are analyzed by immunohistochemistry, or by culturing a patient's tumor cells and examining the cultures for expression of Mammastatin.

In a particularly preferred embodiment, an assay for the diagnosis of breast cancer includes at least two specific antibodies: an antibody to identify the sampled breast tissue as epithelial tissue, such as an anti-cytokeratin antibody, and an anti-Mammastatin antibody. For example, using an immunoblot format, tissue suspected of containing breast cancer cells is homogenized, separated on an SDS/PAGE gel, transferred to membrane, and probed with both anti-keratin and anti-Mammastatin antibodies. Isotype specific second antibodies that are conjugated to a suitable marker system such as peroxidase or alkaline phosphatase are used to detect bound antibodies. Membranes containing bound first and second antibodies are then developed using known colorometric or fluorometric techniques and quantitated by known methods.

In the most preferred embodiment, the sample is analyzed for the phosphorylated forms of Mammastatin, such as by Western Blot, using anti-Mammastatin antibodies. A decline or absence of the high molecular weight (53/49 kD) Mammastatin correlates with advancing breast cancer.

Recombinant Expression Vectors and Transformed Cells

Recombinant expression vectors of the invention are useful for production and amplification of purified Mammastatin protein and portions thereof, and for easy isolation of Mammastatin protein and portions thereof to be used in diagnostic and therapeutic methods.

A target sequence, such as all or a portion of the 2.4 kb Mammastatin cDNA (SEQ ID NO: 1), is cloned into a suitable nucleic acid sequence expression vector such as pUC18, pKC30, pBR322, pKK177-3, pET-3, pcDNA3 (In Vitrogen) for COS and CHO cells, and pAcG3X baculovirus expression vector (PharMingen, San Diego, Calif.) for expression in insect cells, and like, known expression systems by standard methods. Commercially available expression vectors provide for cloning of a target sequence into a site of the vector such that the target sequence is operably linked to transcriptional and translational control regions.

The expression vector is then introduced into suitable host cells using known methods such as calcium phosphate precipitation, liposome mediated transformation, protoplast transformation, electroporation, and the like. Suitable host cells include COS and CHO cells, High 5 and SF9 insect cells, baclovirus, and yeast cells. Other host cells include *E. coli* strains such as *E. coli* DH5α, and avirulent isogenic Salmonella spp. such as *S. typhimurium* deletion mutants lacking adenylate cyclase and cAMP receptor protein, Salmonella mutants in aro genes, and other Salmonella vaccine strains as described in *Bio/Tech,* 6:693 (1988).

Preferably, the cellular host is a Eukaryotic cell, capable of expressing the protein with proper folding and kinase activity to produce a phosphorylated, active inhibitor. Host cells may be screened by transfection with cDNA encoding Mammastatin. Analysis of the protein produced by the transformed cells. e.g. by immunoblot, and the ability of the protein to inhibit mammary cell growth, for example MCF7 cell growth, as described in the examples recited below, can be used to screen potential host cell systems.

Host cells transformed with the target nucleic acid sequence are screened by a variety of methods including colony hybridization or reactivity with antibodies specific for Mammastatin protein. A transformed cell is a suitable host cell carrying a pcDNA3 or other plasmid or vector containing a nucleic acid sequence encoding Mammastatin. One such plasmid is the pcDNA plasmid (pMammB) carrying the 2.4 kb BamHI-XhoI insert from pMammA, deposited with the American Type Culture Collection in 10801 University Boulevard, Manassas, Va. 20110-2209 on Feb. 22, 1996, and was given Accession No. 97451. (See Example 5.)

An expression vector containing the specific target DNA sequence is used to generate all or a portion of Mammastatin protein, by in vitro transcription and translation by insertion into cellular hosts for protein production. Proteins produced from the expression vector system inhibit the growth of mammary cells, normal and cancerous. (See Example 7.) Eukaryotic cells, e.g., Cos7 host cells, transfected with the vector express and secrete Mammastatin into the conditioned medium. Conditioned medium inhibited the growth of normal and cancerous mammary cells. (See Example 8.) Amino Acid Sequence Protein synthesized from the cloned Mammastatin nucleic acid sequence (Seq. ID No. 1) inhibits breast cancer cell (MCF-7) growth.

Recombinant Mammastatin protein can be efficiently produced in purified form and in large quantities. Purified recombinant Mammastatin is useful as a reliable standard for diagnostic assays of the inhibitor in patient samples. Recombinant Mammastatin protein is also useful as a purified therapeutic agent to inhibit or prevent the growth of breast cancer cells.

Therapeutic Use

Mammastatin protein for therapeutic use is produced from NHMC cultures under serum free conditions or by recombinant means. Mammastatin phosphoprotein is used therapeutically to inhibit mammary cell growth, e.g., in the treatment of breast cancer. Preferably, Mammastatin is produced in higher eucaryotic cells to achieve phosphorylation of the protein. Recombinant Mammastatin protein is produced in host cells or by synthetic means.

Functional Mammastatin is administered to patients by known methods, for the administration of phosphoprotein, preferably by injection, to increase inhibitor levels in the bloodstream and increase the inhibitor's interactions with mammary cells.

The protein may be delivered to the patient by methods known in the field for delivery of phosphorylated protein therapeutic agents. In general, the inhibitor is mixed with a delivery vehicle and administered by injection.

The dosage of inhibitor to be administered may be determined by one skilled in the art, and will vary with the type of treatment modality and extent of disease. Since Mammastatin inhibits approximately 50% of mammary cancer cell growth at a concentration of 10 ng/ml and stops growth at about 20–25 ng/ml in vitro, a useful therapeutic dosage range is about 2.5 ug to about 250 ug administered daily dose. Preferred is approximately 125 ug daily administered dose. The aim of the administration is to result in a final body dose that is in the physiological or slightly higher range (50–75 ng/ml). Higher doses of inhibitor (>50 ng/ml) appear to induce apoptosis, as seen in histology of treated cells. For clinical use, the preferred dosage range is about 500 ng/ml for initial treatment of metastatic disease, followed by a maintenance dosage of about 50 ng/ml. Initial clinical studies, reported in the examples below, indicate an administered daily dose of about 50 ng/ml to about 750 ng/ml is sufficient to induce remission in Stage IV breast cancer patients.

Since active Mammastatin is a phosphorylated protein, it is anticipated that multiple doses of the inhibitor will be required to maintain growth inhibiting levels of Mammastatin in the patient's blood. Also, since Mammastatin generally acts as a cytostatic agent rather than a cytocidal agent, it is expected that a maximum effect of the inhibitor will require regular maintenance of inhibitor levels in breast cancer patients.

In its preferred use, Mammastatin is administered in high dosages (>50 ng/ml, preferably about 50–500 ng/ml) to induce tumor regression. Lower, maintenance doses (<50 ng/ml, preferably 20–50 ng/ml) are used to prevent cancer cell growth.

Clinical experience with administered Mammastatin in Stage IV breast cancer patients indicates a useful dose is that which maintains physiological levels of Mammastatin in the blood. Administration is preferably daily, but, may be, for example. by continuous infusion, by slow release depot, or by injection once every 2–3 days. Anecdotal evidence suggests continuous administration may induce feedback inhibition, thus, a preferred administration scheme is to administer daily dose of Mammastatin for approximately 25–28 days, followed by 2–5 days without administration.

Diagnostic Use

Assays of the present invention for detecting the presence of the functional inhibitor in human tissue and serum are useful in screening patients for breast cancer, for screening the population for those at high risk of developing breast cancer, for detecting early onset of breast cancer, and for monitoring patient levels of inhibitor during treatment. For example, analysis of a patient's blood Mammastatin may indicate a reduced amount of high molecular weight, phosphorylated Mammastatin, as compared with a normal control or with the patient's prior Mammastatin profile. Such a change is correlated with increased risk of breast cancer, with early onset of breast cancer, and with advancing metastatic breast cancer. Diagnostic assay for phosphorylated, active, 49/53 kD Mammastatin preferably is by Western blot immunoassay, e.g. ELISA, or using specific anti-Mammastatin antibodies. Screening, for example, in serum, is preferably by immunoassay, e.g., dot blot assay.

For best results, the patient samples should be assayed within a short time of sampling (within one week), stored at 4° C. (less than one year), or frozen for long term storage. Most preferably, samples are frozen until time of assay.

Assay Kit

In a specific embodiment of the invention, an assay kit for the detection of Mammastatin in a patient's fluid and/or breast tissue is provided. The preferred screening assay is an immunoassay such as a dot blot assay to detect or quantitate Mammastatin in blood serum. Such a screening kit includes anti-Mammastatin antibodies and optionally a control antibody and/or Mammastatin controls or standards. A second screening assay analyzes Mammastatin in breast tissue. Preferably, the assay kit contains necessary reagents and tools for reacting the tissue with an antibody to specifically determine that the tissue is breast epithelium, e.g., an anti-cytokeratin antibody, and a specific anti-Mammastatin antibody. The commercially available antibody mixture, pan-keratin (Sigma) is a preferred anti-cytokeratin antibody.

A negative assay for Mammastatin could be caused by either the presence of a breast cancer tumor, or by non-epithelial breast tissue. Use of the anti-cytokeratin antibody guards against false positive assays. Epithelial cells of the breast that do not stain with the anti-Mammastatin antibody or which only express the 44 kD Mammastatin are transformed cells. Thus, by first identifying the tissue as breast epithelium, e.g., isolated from breast tissue and positive with the anti-cytokeratin antibody, and then identifying a second positive reaction with anti-Mammastatin antibody, false positives are avoided.

Because about 30% of the breast cancer cells studied to date express non-phosphorylated inactive, 44 kD Mammastatin, the preferred method of analysis is to differentiate between the 53/49 kD and 44 kD forms, e.g. by Western blot analysis.

The invention is further defined by reference to the following examples:

EXAMPLE 1

Human Mammary Cell cDNA Library

A cDNA library was prepared from human mammary cells obtained from reduction mammoplasties (UM Hospital). Total RNA was isolated from the mammary cells by cesium chloride gradient. From the total RNA preparation, mRNA was isolated. The methods used were those described in Garner I., "Isolation of total and poly A+ RNA from animal cells", *Methods Mol. Biol.* (1994) 28:41–7.

Reverse transcriptase in the presence of the isolated mRNA produced cDNA that was then ligated to EcoRI linkers. The cDNA was inserted into EcoR1 cut T4 DNA ligase-treated Lambda Zap, and amplified in XL1-blue *E. coli*, following the method described in Short J M., et al. (1988) *Nucleic Acids Research* 16: 7583.

EXAMPLE 2

Preparation of Mammastatin Oligonucleotides

The normal human mammary cell cDNA library prepared in Example 1 was screened for the presence of nucleic acids encoding Mammastatin using degenerate oligonucleotides. The degenerate oligonucleotides were derived as follows:

Normal human mammary cells were obtained from the Plastic Surgery Department of the University of Michigan Hospital or from the Cooperative Human Tissue Network. The tissue was reduced by collagenase treatment generally following the procedure described in Soule, et al., *In Vitro*, 22:6 (1986).

Mammary cells were grown to confluence in 175 cm² flasks in DMEM/F12 low calcium media formulated with 40 μM $CaCl_2$ and supplemented with 5% CHELEX treated equine serum (Sigma), 0.1 μg/ml cholera toxin (Sigma), 0.5 μg/ml hydrocortisone (Sigma), 10 ng/ml epidermal growth factor (EGF, Collaborative Research, Bedford Mass.), 10 μg/ml insulin, and 1 μg/ml penicillin/streptomycin following the method described in Soule, et al., *In vitro* 22:6(1986). Equine serum was treated with CHELEX resin for three hours at room temperature to remove serum calcium.

Cell lysates were prepared by rinsing cells with TBS and scraping from the flask with a Teflon scraper. Cells were collected by centrifugation and lysed with 8M Urea, 50 mM TRIS pH 7.5, 0.5% Beta-mercaptoethanol, 0.5% TRITON X-100 (lysis buffer) and three minutes of sonication on ice.

The cell lysates were fractionated on DEAE-Sephacel anion exchange resin (Sigma) equilibrated with lysis buffer. Lysates were loaded onto the resin filled columns (50 ml disposable, Bio Rad) and washed with ten column volumes of the lysis buffer. Material flowed through the columns with only gravity feed. Fractions were eluted with a salt gradient produced by continuous gravity feed of elution buffer containing 5M NaCl into a closed mixing chamber initially containing elution buffer (250 ml of 8M urea and 50 mM TRIS pH 7.5) in the absence of salt.

Elution fractions (2 ml) were collected with a Gibson fraction collector, and were analyzed for the presence of mammary cell growth inhibitor by dot blot with the anti-Mammastatin antibody, 7G6, described above.

Positive fractions were pooled and dialyzed into lysis buffer with 50 mM NaCl, and were again separated on an identical ion exchange column and eluted with a continuous decreasing pH gradient (pH 8 to pH3) in elution buffer with 50 mM NaCl. (To produce the pH gradient, pH3 buffered urea was continuously mixed with the initial pH8 buffer.) Fractions (2 ml) were collected and analyzed with the 7G6 antibody as described above.

Positive fractions were again pooled and concentrated to ⅒ the original volume by filtered centrifugation (Amicon Centriprep, 10 kD cutoff). The concentrated pool was size fractionated by preparative SDS polyacrylamide gel electrophoresis (PAGE) along with prestained molecular weight standards (Sigma).

Protein contained in the molecular weight range between 40 and 60 kD was excised from the gel in 0.5 cm strips or fractions. Electroelution of the protein from each gel strip was carried out by placing the gel strip in 1 ml of running buffer (192 mM glycine, 25 mM TRIS pH 8.3, 0.1% SDS) in dialysis tubing. The tubing was placed in a submarine electrophoresis apparatus and electroeluted overnight at 25 volts. Current was reversed for 2 minutes and running buffer, now containing the electroeluted protein, was removed. Purity of the eluted protein was checked by analytic SDS PAGE with silver-staining, and also by immunoblot with the 7G6 antibody, following the procedure described in Towbin et al., *J. Clin. Chem. Clin. Biochem.* 27:495–501 (1989). Fractions that were at least 70% pure as determined by silver-stained PAGE were pooled, concentrated, and lyophilized to powder form.

The pooled protein was cleaved with cyanogen bromide by resuspending lyophilized powder in 500 μl of 70% formic acid and incubating overnight at room temperature (about 20 hours) with 20 mg/ml of cyanogen bromide (Sigma). The methods used are described in Freemont, et al., *Arch. Biochem. Biophys.* 228:342–352 (1986). Cyanogen bromide-cleaved protein samples were dialyzed into double distilled, deionized water and again concentrated and lyophilized to powder.

Cyanogen bromide cleavage generated multiple peptides from the original protein sample, which were separated by preparative 15% SDS PAGE and transferred onto PVDF membrane by electroelution.

In addition to the protein obtained from mammary cell lysates, protein was also isolated from normal human mammary cell conditioned medium. Normal cells were incubated with 8 ml DMEM lacking phosphates and supplemented with 200 μCi/ml $^{32}$P-ortho-phosphate and 1% dialyzed fetal bovine sera. Cells were allowed to grow for 24 hours in the presence of the $^{32}$P before conditioned media was collected.

The collected conditioned media was concentrated 5× by Amicon filtration with 10 kD exclusion limit. Concentrated media was rinsed once with PBS on filtration membranes to remove excess unincorporated phosphate and was further fractionated by S-200 SEPHACRYL (Pharmacia, Upsala, Sweden) molecular sieve chromatography (100 cm×0.75 cm column) eluted with PBS. Both the filter and the column permit removal of unincorporated $^{32}$P from the sample. One ml fractions were collected from the column, and labeled fractions identified by scintillation counting. Radioactive fractions were pooled and analyzed by SDS PAGE with silver staining and autoradiography. The pooled protein was concentrated, lyophilized to powder, and combined with the larger mass of unlabeled protein purified as described above, before cyanogen bromide cleavage. The addition of labeled protein provided a convenient means of tracing cyanogen bromide cleavage fragments containing phosphorylated Mammastatin peptides. Cleaved peptides were separated on preparative PAGE as described above.

After radioactive proteins were cyanogen bromide cleaved, separated, transferred to PVDF membrane, and exposed to Xray film, two labeled bands of approximately 20 and 22 kD were seen. These two peptides were excised from membranes and sequenced by Edman degradation methods at the University of Michigan Biomedical Research Core Facility using methods described in Ullah Alt et. all., *Biochem. Biophys. Res. Comm.* 203:182–189 (1994). The amino acid sequences of each of the two peptides was compared with known database sequences using the NIH "BLAST" server. The two peptides appeared to be unique.

A particularly unique portion of each sequence was used to produce degenerate oligonucleotides, using the standard third position degeneracy according to the method described in Jerala, *Biotechniques* 13:564–567 (1992). From the 20 kD peptide, the sequence "gly-gln-leu-glu-tyr-gln-asp-leu-arg" (Seq ID No. 2) was used; from the 22 kD peptide, the sequence "tyr-glu-arg-asp-leu-lys-gly-arg-asp-pro-val-ala-ala" (Seq ID No. 3) was used to generate multiple species of oligonucleotides. The degenerate oligonucleotides were purified by high pressure liquid chromatography.

| SEQ. ID NO. | Peptide |
|---|---|
| 2 | gly gln leu glu tyr gln asp leu arg |
| 3 | tyr glu arg asp leu lgs gly arg asp pro val ala ala |

The degenerate oligonucleotides were end-labeled with $^{32}$P-gamma ATP and T4 DNA polynucleotide kinase (BRL, Bethesda, Md.) and resuspended in T4 DNA kinase buffer (60 mM TRIS pH 7.8, 10 mM $MgCl_2$, 15 mM beta-mercaptoethanol) at 1.5 mg/ml. Oligonucleotides (250 μM) were then incubated with 0.33 μM ATP, 5 units kinase in 25 μl kinase buffer, for two hours at 37° C. Incorporation of $^{32}$P-phosphate was determined by TCA precipitation (15% TCA, 4° C., 15 minutes). Typical incorporation was 10$^9$ cpm/μg DNA.

EXAMPLE 3

Screening Mammary Cell cDNA Library With Degenerate Oligonucleotides

Bacteria infected with phage prepared for Example 1, containing a normal mammary cell cDNA insert, were plated on 15 cm NZCYM (10 g, NZ amine (Bohringer Manheim), 5 g NaCl, 5 g yeast extract, 2 g $MgSO_4$, 1 g casamino acids) plates in top agar (1/10 dilution of infected bacterial cultures to 6 ml of 7% NZYM top agar) and allowed to incubate eight hours at 37° C. Plates containing plaques were overlaid with nitrocellulose for 15 minutes before denaturation of phage. Phage was denatured by blotting filters (DNA side up) on Whatman paper saturated with 0.5 M NaOH. 1.5 M NaCl for 5 minutes. Filters were rinsed with $H_2O$ before incubating for 5 minutes in 1 M TRIS pH 7.0, 1.5 M NaCl followed by 20×SSC and 2×SSC, each for 5 minutes. Filters were dried and baked for 1 hour at 80° C. or placed under ultraviolet light to immobilize DNA. Baked filters were washed for 30 minutes in 2×SSC with 1% SDS and then prehybridized with 50% deionized formamide, 5×Denhart's solution, 1% SDS, 5×SSC and 100 μg/ml sheared salmon sperm DNA overnight at 37° C.

Filters were hybridized with the labeled degenerate oligonucleotide prepared as described for Example 2 in prehybridization buffer to which 10$^7$ cpm/ml of heat-denatured (95° C., 5 minutes) labeled degenerate oligonucleotide had been added. Hybridizations were performed at 37° C. for 24 hours. Filters were washed with 2×SSC for thirty minutes at 37° C. followed by 3 washes in 2×SSC plus 1% SDS at 50° C. for thirty minutes. Filters were rinsed with 2×SSC briefly, dried and exposed to Kodak AR-5 film for 24–48 hours to identify positive plaques.

Positive plaques were isolated from agar plugs excised using a reversed 200 μl sterile pipette tip, and resuspended in SM buffer overnight at 4° C. Secondary and tertiary plates (10 cm) were made using XL1-B infected with 1/10,000 dilution of phage containing SM buffer, to bacteria, in NZCYM (with 1 mM MgSO4). Plaques were produced by incubating infected bacteria for 8 hours as described above, and were then transferred to nitrocellulose before screening with labeled degenerate oligonucleotides. Screening was performed essentially as described in Kroczek R A., *J Chromatogr* 618:133–45(1993), using 10$^7$ cpm/ml of labeled DNA for hybridizations and a final wash stringency of 2×SSC at 50° C. for thirty minutes.

The clone selected for further analysis was one recognized by both of the degenerate oligonucleotides. This clone was given the name "pMammA".

EXAMPLE 4

Sequencing of Mammastatin cDNA

The positive clone obtained in Example 3, pMammA, was sequenced by an automated sequencer at the Biomedical Research Core Facility at the University of Michigan and also by dideoxy DNA sequencing using 15% DNA sequencing gels and radiolabeling the DNA fragments with $^{35}$S nucleotides. The methods used are described in Lasken R S., et al. *Proc Natl Acad Sci USA* 82:1301–5 (1985). The nucleic acid sequence obtained is shown below in Table 1 (Seq ID No. 1).

The recognized error rate of automatic sequences is about 5%. Therefore, the clone deposited is resequenced for confirmation of the nucleotide sequence, particularly mindful of areas suspected of potential errors, as noted.

EXAMPLE 5

Subcloning the Mammastatin cDNA into an Expression Vector

The Mammastatin cDNA insert, pMammA, was subcloned into the expression vector, pcDNA 3 (In Vitrogen). The Mammastatin cDNA was isolated by digesting the pMammA plasmid obtained as described for Example 4 with BamH1 and Xho1 restriction endonucleases. The restriction enzymes cut the plasmid at the ends of the Mammastatin clone insert, creating a linear plasmid fragment and a linear insert fragment. The digested sample was placed in the wells of a 1.2% agarose gel submerged in an electrophoresis apparatus, a 50V current was applied for two hours. Electrophoresis separates DNA fragments on the basis of size with the larger plasmid DNA fragment having the slower migration rate on the gel. The portion of the agarose gel containing the 2.4 kb was visualized by ethidium bromide staining and observing the gel over an ultra-violet light box. The 2.4 kb Mammastatin fragment was cut from the gel and placed into dialysis tubing and the DNA was electroeluted into tris-borate buffer, TBE: (0.089M Tris-borate, 0.089M boric acid, 0.002M EDTA) that was collected and precipitated with ethanol.

The pcDNA3 plasmid DNA was modified to accept the Mammastatin cDNA fragment during ligation. pcDNA3 plasmid was digested with BamH1 and Xho1 restriction endonucleases and after digestion was complete, the DNA was incubated for one hour in the presence of calf intestinal phosphatase to remove 5' phosphates. The pcDNA3 sample was then phenol extracted and ethanol precipitated.

The pcDNA3 and the Mammastatin 2.4 kB cDNA fragment were ligated together. The 2.4 kB Mammastatin fragment and the linear pcDNA3 plasmid were mixed in a 3:1 ratio in the presence of T4 DNA ligase. The ligation reaction was allowed to incubate for one hour and then stored at 4° C. overnight. After the ligation reaction was completed the DNA was used to transform *E. coli* competent cells. Subcloning was verified by purifying plasmid DNA from ampicillin selected colonies. The plasmids were digested with the restriction endonucleases BamH1 and XhoI. The digested DNA samples were placed in an agarose gel and separated by electrophoresis. A plasmid containing the correct size Mammastatin DNA fragment was designated pMammB, and was deposited with the American Type Culture Collection (ATCC) on Feb. 22, 1996, and given accession number: ATCC 97451.

EXAMPLE 6

Transfection and Protein Expression from the Mammastatin cDNA Sequence

Cos-7 cells do not express immunoreactive proteins that co-migrate with the Mammastatin proteins. pMammB and PCDNA3 were used to transfect Cos-7 monkey fibroblast cells using LIPOFECTIN® (BRL, Life Technologies, Bethesda, Md.) using the manufacturers suggested protocol. The transfected cells were grown for two days prior to harvest. Transfected cells were removed from plates by trypsinizaton of cells using standard protocols. (2.5 ml's of Trypsin (0.25% SIGMA) was incubated in flasks of cells at 37° C. for 5 minutes. A 7.5 ml aliquot of RPMI media with 10% FBS (fetal bovin serum) was added and cells were collected by centrifugation.) Cells were counted by hemocytometer and lysed in SDS PAGE sample loading buffer at $10^7$ cells/ml. Cell lysates were separated on 8–15% SDS-PAGE gradient gels (Biorad) and transferred to a nylon membrane using methods described in Towbin H., et al., *J. Clin Chem Clin Biochem* (1989 August) 27(8):495–501. The membrane was probed with anti-Mammastatin monoclonal antibody 7G6. Bound antibody was detected with peroxidase conjugated GAM-IgM and developed by ECL (Amersham).

As shown in FIG. 1, Cos-7 cells transfected with pMammB (lanes C,D) expressed immunoreactive proteins that co-migrated with Mammastatin protein (lane A). Cos-7 cells transfected with the empty vector PCDNA3 alone did not express immunoreactive proteins when immunoblot experiments were performed (lane B).

| DNA/AA SEQUENCE | |
|---|---|
| Lane A | NHMC (25 µg) - control |
| Lane B | Cos pcDNA3 cell lysate (25 µg) - control |
| Lane C | Cos-pMammB cell lysate (10 µg) |
| Lane D | Cos-pMammB cell lysate (20 µg) |

The immunoblot experiments illustrate the pMammB clone contains a cDNA insert capable of synthesizing a protein with the size and immunologic characteristics of Mammastatin. In addition, immunoreactive proteins of 44, 49 and 53 kD were expressed in Cos-7 cells transfected with pMammB. These proteins migrated at the same molecular weight as the Mammastatin proteins previously identified in normal human mammary cells. This group of immunoreactive proteins was not identified in Cos-7 cells transfected with the empty vector, pcDNA3.

In the particular assay shown in FIG. 1, the NHMC control shows an unusually high amount of 44 kD Mammastatin. This is an artifact produced by long term (>1 yr) storage of the NHMC standard at 4° C., causing degradation of the higher molecular weight forms, over time. When fresher NHMC samples (<1 yr old) or frozen samples are used, the 44 kD protein is always less abundant than the higher molecular weight forms.

EXAMPLE 7

GST Fusion

The Mammastatin clone can be similarly subcloned into a baculovirus expression system. The pMammA insert has been subcloned into a pAcG3X vector obtained commercially from Pharmgen (San Diego, Calif.). This vector allows production of Mammastatin as a fusion protein with glutathione S-transferase (GST), having a portion of the GST gene upstream of the coding site.

The pMammA insert was subcloned by preparing sets of PCR primers that contained Bam H1 (5') and Sma 1 (3') restriction enzyme recognition sites, a small, non-specific region, and a portion of the Mammastatin sequence. Three sets of primers, each shifted in reading frame, were prepared. The primers hybridized to the pMammA clones and in a typical PCR reaction with pMammA template DNA, amplified a pMammA PCR product capable of insertion into the reading frame of the GST gene in pAcG3X. The vector was then used to transfect High 5 (In Vitrogen) host insect cells, and express a GST-Mammastatin fusion protein that was easily purified from host insect cells using glutathione resin (glutathione agarose, Qiagen, Chatsworth, Calif.).

To prepare DNA for insertion into the BamH1, Sma 1 restriction site of pAcG3X (ParMingen, San Diego, Calif.), primer sets were prepared in three reading frames to include, for the 5' primer, the BamH1 recognition site (GGATCC), a portion of the pMammA sequence, and some 5' sequence from the pBluescript vector. The 3' primers were identical, and included the SmaI recognition sequence (GGG CCC), a portion of the pMammA sequence, and some pBluescript sequence.

The primer sets used are shown in the following table:

| Seq. ID No: | 5' Primers (in three reading frames)* |
|---|---|
| 4 | 5'-TG<u>G GAT CCC</u> TTC GCC ACG AGC ACG GTG-3' |
| 5 | 5'-TG<u>G GAT CCT</u> TCG CCA CGA GCA CGG-3' |
| 6 | 5'-TG<u>G GAT CCC</u> CTT CGC CAC GAG CAC-3' |
|  | 3' Primer |
| 7 | 5'-TTT TTT TTT TTT <u>GGG CCC</u> TTA AGT-3'** |

*Bam H1 site underlined
**Sma 1 site underlined

Figure 2:
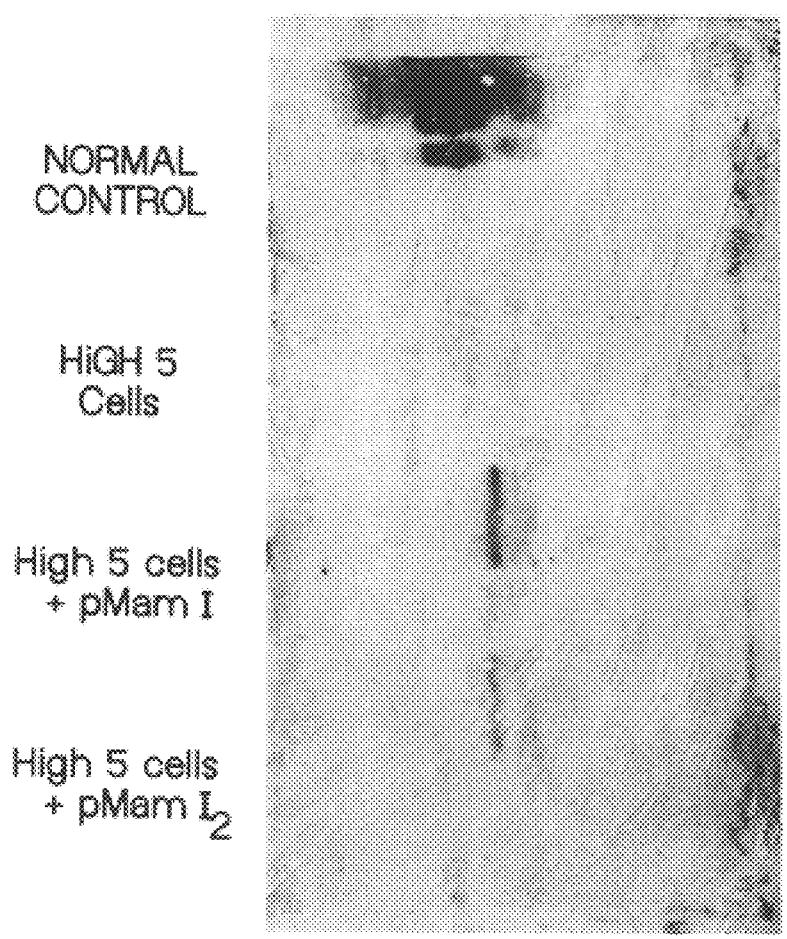
FIG. 2 is an immunoblot showing expression of Mammastatin in insect cells.

Only one primer set (Seq. ID NOS. 5 and 7) produced clones capable of coding for active inhibitory Mammastatin. The active clones, when used to transform High 5 cells, produced Mammastatin that was immunologically reactive in the transformed cells (see FIG. 2).

Other known eukaryotic expression systems may similarly be used to produce Mammastatin protein.

EXAMPLE 8

Figure 3A:
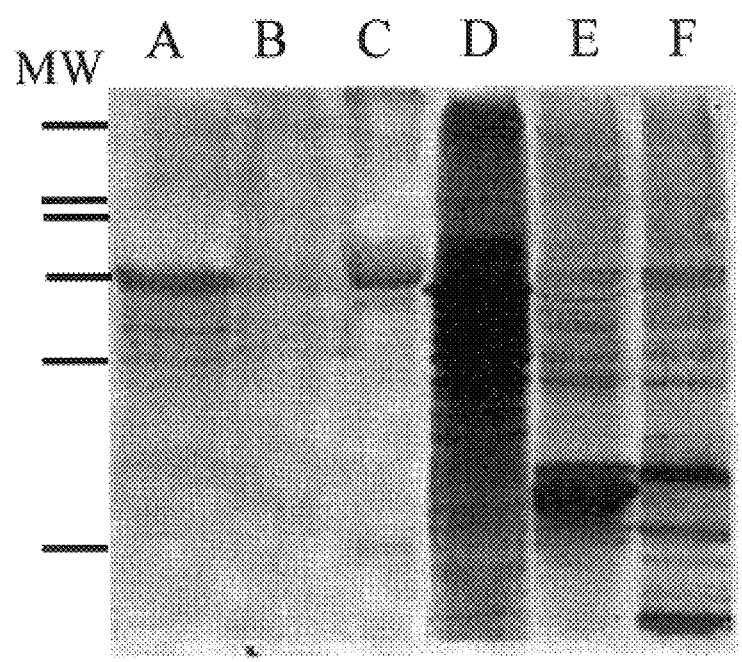
FIG. 3A is an autoradiograph showing expression of recombinant Mammastatin produced by in vitro transcription and translation and used in the growth inhibition assays of FIG. 3B.

Inhibition Assay with Proteins Produced by In Vitro Transcription and Translation In vitro transcription of pMammB, Mammastatin cDNA was performed using a Stratagene, Express RNA transcription kit to produce Mammastatin RNA. The RNA produced was translated into protein using the Stratagene In Vitro Express translation kit (see FIG. 3A). Mammastatin protein produced from translation of the Mammastatin RNA was shown to inhibit mammary cell growth in culture.

Cultures of MCF-7 cells were treated with protein products produced in the translation assays described above. Protein products (5% by volume, culture medium) were added to cells in 12-well plates containing 1 ml medium per well. Parallel cultures were treated with both the translation product and the anti-Mammastatin antibody 3C6, at 30 µg/ml final concentration.

As a negative control, cultures were treated with protein products translated with the Stragene In vitro Express Translation kit incubated in the absence of Mammastatin cDNA (i.e. employ vector). These lysates do not have the proper machinery to produce the Mammastatin protein.

All cultures were allowed to grow for six days after being treated with the protein products and the cell number of each sample was calculated using a Coulter counter. There were triplicate samples of each culture condition so that the cell number of each sample was averaged and percent inhibition was determined by comparison to the reticulocyte lysate treated control cells.

Figure 3B:
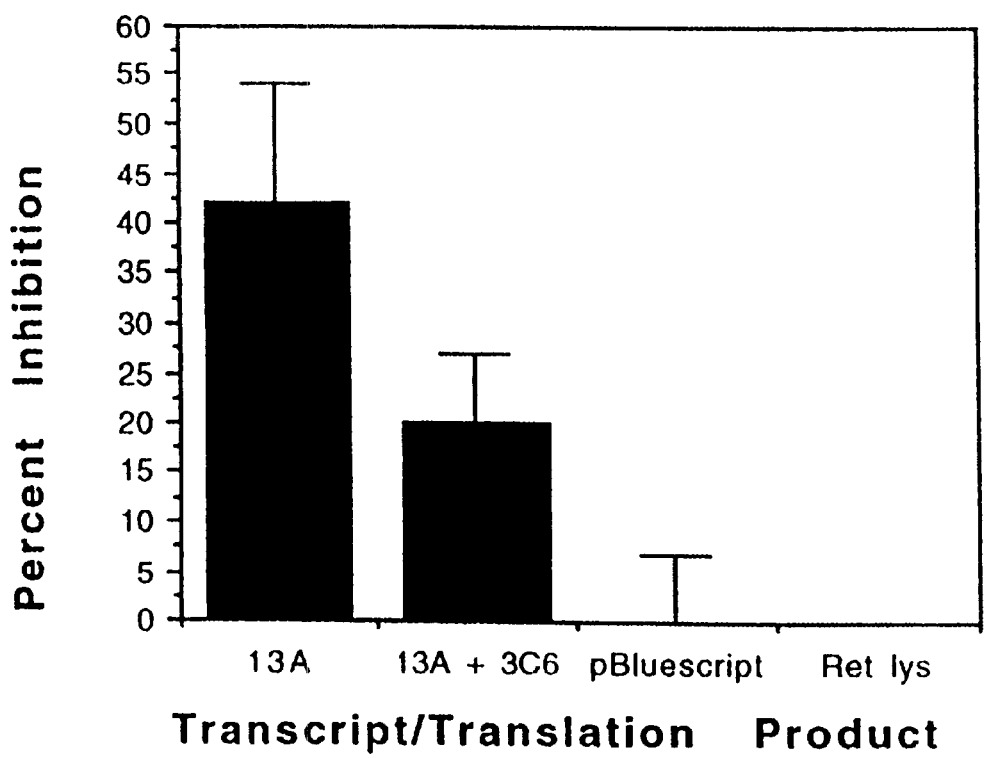
FIG. 3B is a graph showing inhibition of mammary cell growth by recombinant Mammastatin produced by in vitro transcription and translation.

As shown in FIG. 3B, the protein translation product of pMammB inhibited MCF-7 cell growth. This inhibition was greatly reduced or blocked in the presence of anti-Mammastatin antibody, 3C6.

EXAMPLE 9

Inhibition Of Mammary Cells with Proteins Present within Conditioned Media Obtained From Growing Cos-7 Cells Transfected with pMammB Mammary cell growth inhibition experiments were performed using conditioned media obtained from Cos-7 cells transfected with pMammB as described for Example 6. Mammastatin is a secreted protein and is found in conditioned media of cells expressing the protein. The growth inhibition caused by conditioned media was blocked by the addition of anti-Mammastatin antibody.

MCF-7 cells were plated at $10^4$ cells/ml in MEM supplemented with 10% non-essential amino acids and FBS (SIGMA). Cells were allowed to attach overnight and were then supplemented with 10% by volume of conditioned media (3 day culture) from either: (1) Cos-7 cells transfected with the empty vector pcDNA (Negative control), (2) Cos-7 cells transfected with pMammB (pMammB-Cos), (3) NHMC-conditioned media, or (4) non-conditioned media. Parallel MCF-7 cultures were supplemented with 30 ug/ml of 3C6 blocking antibody. Treated MCF-7 cells were allowed to grow for six days and were then counted by hemocytometer.

Figure 4:
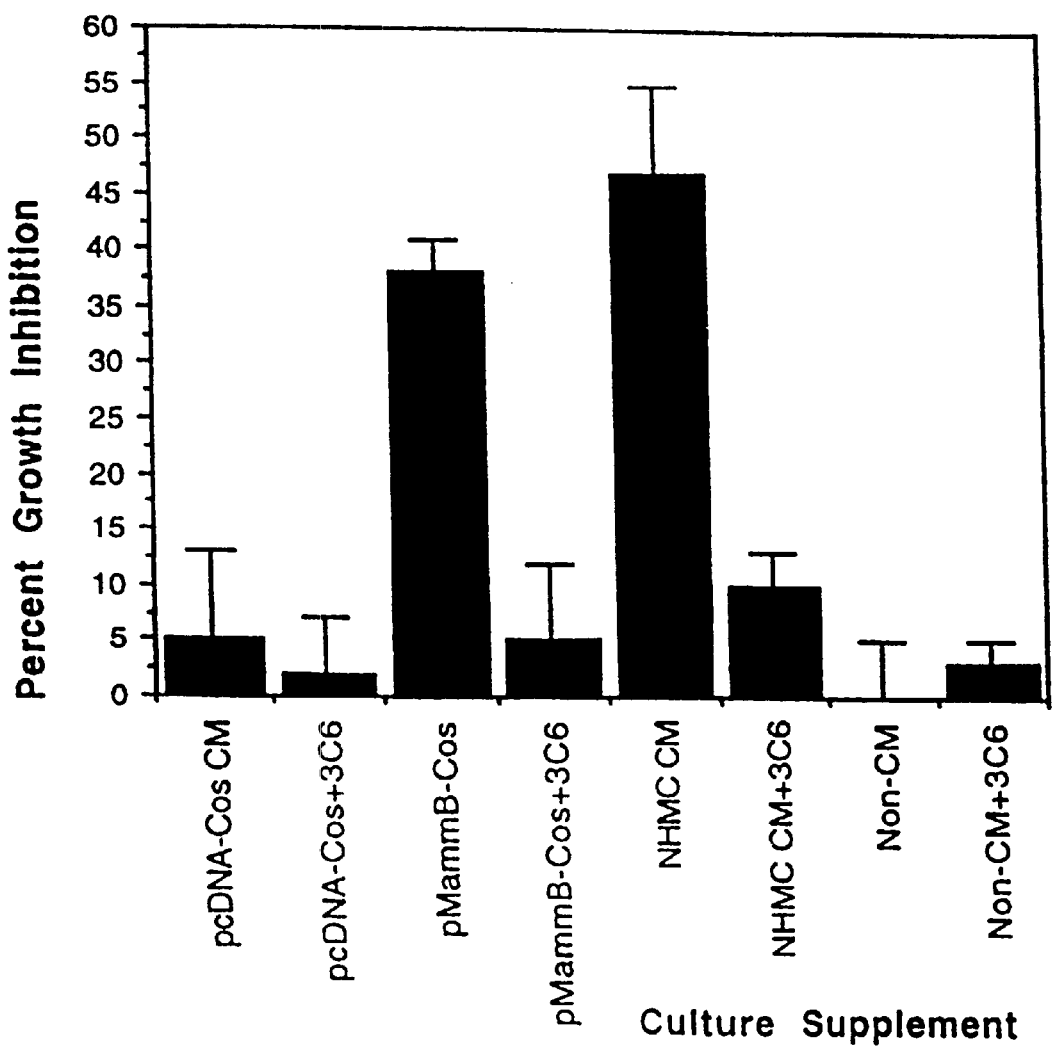
FIG. 4 is a graph showing growth inhibition in human mammary cancer cell growth by treatment with conditioned medium of Cos-7 cells transfected with Mammastatin cDNA.

Inhibition of cell growth was determined by comparing the growth of MCF-7 cells incubated in conditioned media with the growth of MCF-7 cells incubated in control, non-conditioned media. Data are shown in FIG. 4, and demonstrate that conditioned media from pMammB-transformed cells inhibited mammary cancer cell growth as efficiently as did normal human mammary cell conditioned media. This inhibition was blocked in the presence of anti-Mammastatin antibody.

EXAMPLE 10

Three Immunologically Reactive Anti-Mammastatin Proteins

Whole normal human mammary cells (NHMC) and mammary carcinoma cells in tissue culture cells were lysed, and cell lysate proteins were separated by SDS/PAGE as described above and in Ervin, Paul, 1995, Doctoral dissertation, University of Michigan, Chapter 2. Lysed cell samples were separated on 10% SDS-PAGE in a Mini-Protean II apparatus (25 µg/sample). Proteins were transferred to nitrocellulose and probed with the anti-Mammastatin monoclonal antibody 7G6 or IgM control antibody, alkaline phosphatase conjugated second antibody, goat anti-mouse IgM was utilized with an NBT/BCIP substrate system to detect positive antibody reactions colorometrically. The data are shown in FIG. 5.

| CARCINOMA CELLS | |
| --- | --- |
| LANE 1 | ZR-75-1 |
| LANE 2 | MDA MB 435 |
| LANE 3 | 4MCF-7 |
| LANE 4 | T47D |
| LANE 5 | NHMC-14 positive control |
| LANE 6 | NHMC-14 positive control with the 38C13 antibody |
| NORMAL CELLS | |
| LANE 7 | NHMC-17 |
| LANE 8 | NHMC-16 |
| LANE 9 | NHMC-15 |
| LANE 10 | NHMC-14 |
| LANE 11 | NHMC-6 |
| LANE 12 | NHMC-14 positive control |

Figure 5:
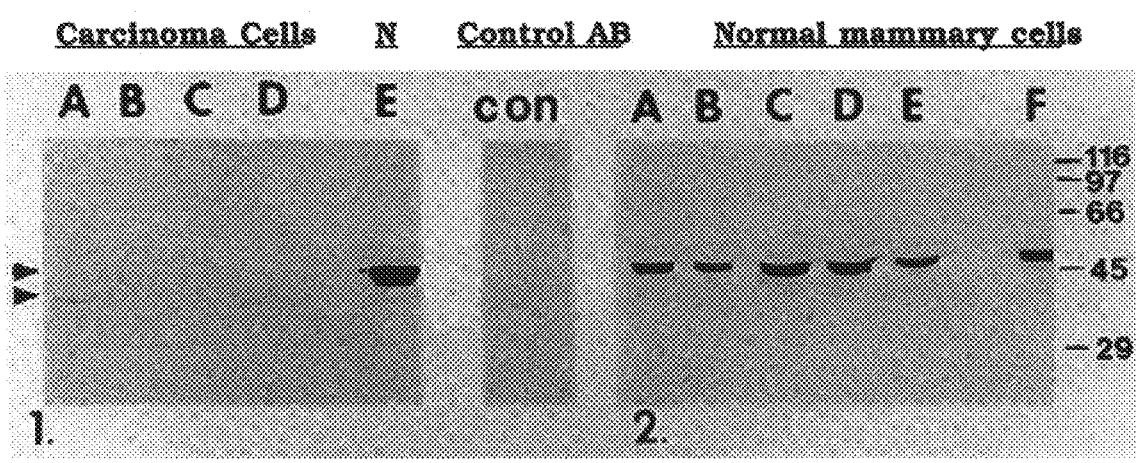
FIG. 5 is a Western Blot showing relative amounts of 53, 49 and 44 kD Mammastatin in normal and cancerous human mammary cells.

As shown in FIG. 5, normal human mammary cells expressed a doublet of proteins migrating at 49 and 53 kD that were strongly recognized by the anti-Mammastatin monoclonal antibody and a third weakly immuno-reactive 44 kD protein. The four tumor cell lines tested expressed either a 44 kD immuno-reactive protein alone (lanes 1,4) or no immunoreactive protein at all (lanes 2, 3).

The above data is representative of experiments performed on normal cells from 42 different reduction mammoplasty patients over a period of several years. Expression of the 44 kD protein in normal cells and cancer cell lines varied in intensity with each preparation.

EXAMPLE 11

Mammastatin is a Phosphoprotein

Cellular phosphorylated proteins of mammary cells were labeled with $^{32}P$ by supplementing normal mammary cell cultures with $^{32}P$-orthophosphate (200 µCi/ml) for 24 hours. Conditioned media was concentrated 5× by Amicom Centrifugation with a 30 kD molecular weight restriction. Concentrated media was rinsed once with PBS on filtration membranes to remove excess unincorporated phosphate and fractionated by S-200 SEPHACRYL (Pharmacia, Upsala, Sweden) molecular sieve chromatography (100 cm×0.75 cm column) with PBS elution buffer. Immunoblots were prepared as described above and probed with the 7G6 antibody.

A radiolabeled 53 kD Mammastatin protein was identified in conditioned media by immunoprecipitation. This analysis indicated Mammastatin is a secreted phosphoprotein. Since secreted phosphoproteins are uncommon, Brefeldin A treatment of cells was utilized to determine whether Mammastatin was present in conditioned media due to secretion or to cell breakage or leaking. Brefeldin A is a fungal compound that blocks the secretion of proteins from eukaryotic cells. Brefeldin A inhibits normal endoplasmic reticulum and golgi function and blocks vesicle formation (Ervin, Paul, 1995, Dissertation, Page 25). Since most secreted proteins are liberated from the cell by is a process of exocytosis from membrane bound vesicles, blocking vesicle formation blocks secretion of many proteins. When NHMC are grown in the presence of Brefeldin A, phosphorylated Mammastatin is not identified in conditioned media.

To determine the amino acid residues that are phosphorylated in Mammastatin protein, radiolabeled 53 kD protein was subjected to phospho-amino acid analysis. NHMC cells were incubated with $^{32}P$-orthophosphate for 24 hours. Cell lysates were then immunoprecipitated with the anti- Mammastatin antibody 7G6 and purified as follows. The 53 kD protein was digested with trypsin and hydrolyzed with acid. Two dimensional thin layer chromatography was used to analyze the phosphorylated amino acids of Mammastatin. $^{32}$P-amino acids were mixed with phospho-ser/thr/tyr controls and loaded at the origin (0) of a 2D TLC plate (20 cm). The samples were separated into two dimensions: 1st dimension—pH 1.9 Buffer (50 ml formic acid, 156 ml glacial acetic acid/2000 ml (1794 H$_2$O), 20 minutes @ 1.5 K volts;

rotate clockwise; 2nd dimension—pH 3.5 Buffer (10 ml pyridine, 100 ml's glacial acetic acid: 1890 ml H$_2$O) for 16 minutes @ 1.3 K volts.

The TLC plates were stained with ninhydrin and exposed to film. Phospho-amino acid analysis demonstrated the 53 kD Mammastatin protein contained three types of phosphorylated amino acid residues by comparing autoradiographs to ninhydrin stained phospho-amino acid standards.

Threonine (Th) was the most abundant phosphorylated amino acid followed by serine (S) and Tyrosine(Ty), the least abundant phosphorylated species. However, the relative abundance of phosphoamino acid residues may not be representative of that in the native protein, since acid hydrolysis can free phosphate from phosphotyrosyl residues.

EXAMPLE 12

One Mammastatin Protein with Varied Phosphorylation

Cellular phosphorylation of proteins can be modulated by phosphatases and kinases. Mammastatin is differentially phosphorylated in normal and tumor cell lysates due to differential activities of Mammastatin phosphatases. The effect of phosphatase on Mammastatin in NHMC lysates was examined.

Figure 6:
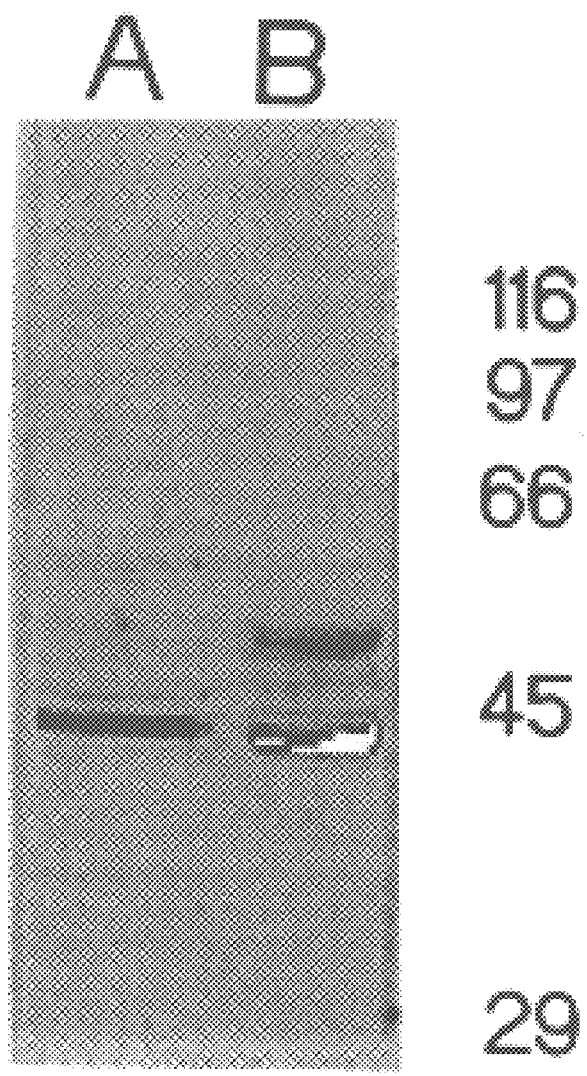
FIG. 6 is an immunoblot showing phosphatase digestion of Mammastatin.

NHMC were grown to confluence in low calcium media and collected by scraping into TBS. Cells were washed with TBS and resuspended at 2 mg/ml in acetate buffer pH 6.6 with 0.5% Triton X-100.5 µg/ml of either Yersinia phosphatase (YOP)(Stuckey, et al., Nature 370:571–5 (1994)) or Yersinia phosphatase mutant (MYOP) containing an active site mutation was used to digest cell lysates for six hours at 37° C. (YOP and MYOP were gifts from Dr. S. Jack Dixon, University of Michigan, Biochemistry Department). As shown in FIG. 6, digestion of normal human mammary cell lysates with Yersinia phosphatase (YOP) resulted in a reduced amount of 53 kD Mammastatin protein identified by anti-Mammastatin immunoblot (lane A). In contrast, digestion with the Yersinia phosphatase mutant (MYOP, lane B), did not alter identification of the 53 kD Mammastatin protein. These results indicate identification of the 53 kD Mammastatin protein by immunoblot is a convenient measure of the state of phosphorylation of the Mammastatin protein.

Figure 7:
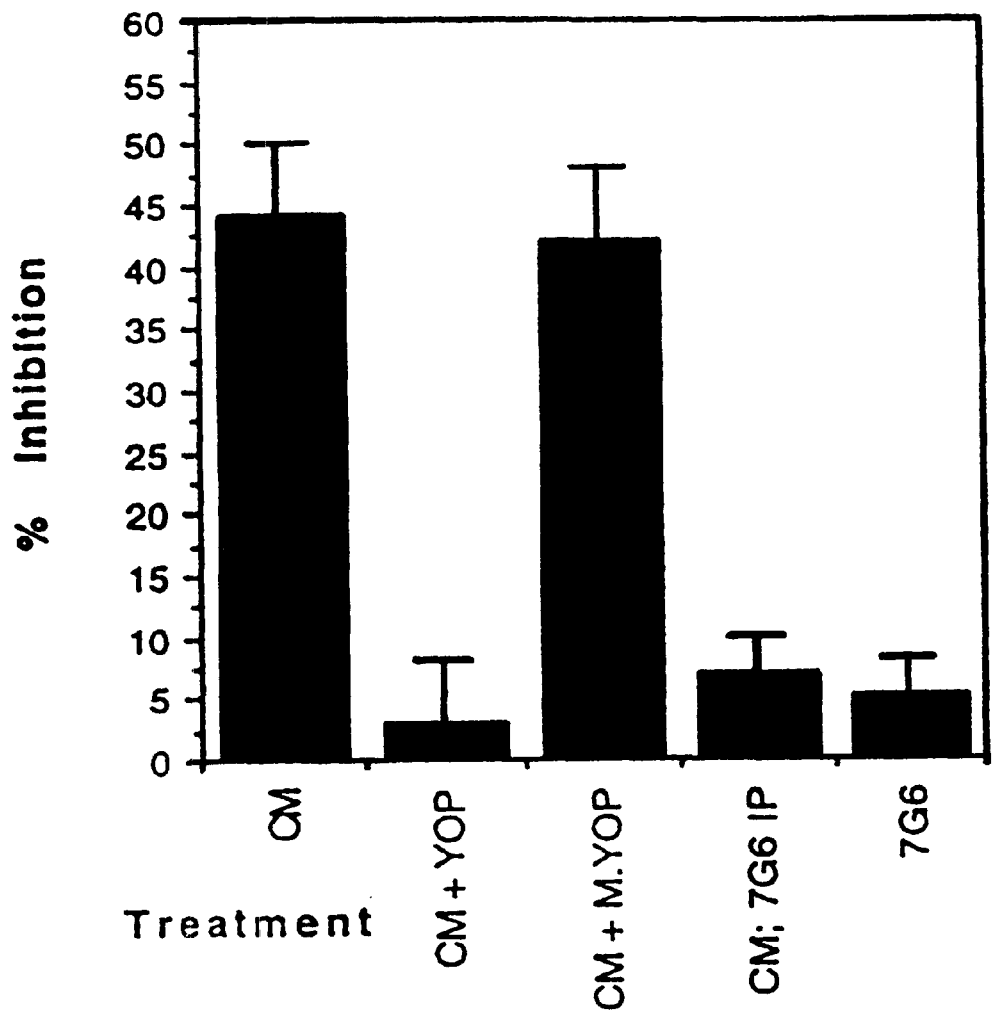
FIG. 7 is a graph showing the effect of Phosphatase on the activity of Marnmastatin.

Conditioned medium incubated in the presence of Yersinia phosphatase (YOP), as described above, was used to treat MCF-7 cells. As previously observed, NHMC conditioned medium inhibits the growth of MCF-7 cells, and this inhibition is blocked by anti-Mammastatin antibodies. As shown in FIG. 7, treatment of NHMC conditioned medium with YOP abrogates this inhibitory activity. As a control, treatment of NHMC conditioned media with a YOP mutant lacking phosphatase activity (M.YOP) was tested. This mutant had no effect on the inhibitory activity of NHMC conditioned media. Immunoprecipitation of the conditioned media with the anti-Mammastatin antibody 7G6 removed the inhibitory activity.

TCA precipitation indicated that incubation of conditioned media with YOP removed about 50% of incorporated phosphate. As shown above, YOP also removed the 53 kD species from NHMC lysates (FIG. 6).

EXAMPLE 13

Phosphorylated Mammastatin Produced by Normal But Not Cancerous Mammary Cells Normal and transformed mammary cells were labeled with $^{32}$P orthophosphate. Carcinoma cell lines were grown in the media as suggested by the ATCC, with the exception of MCF-7 cells which were grown in MEM (Celox) supplemented with 10% FBS, non-essential amino acids, and insulin (10 mg/l). $^{32}$P-orthophosphate labeling of cellular proteins was performed in phosphate-free DMEM (ICN) containing 2% dialyzed FBS. Cells were incubated 24 hours at 37° C. with 200 µC:/ml of $^{32}$P-phosphate. After 48 hours, conditioned media was collected from cell cultures and concentrated 5×. Conditioned media was washed with TBS and concentrated on Amicon filters with a 10 kD mw cut-off. The cell layer was scraped (using a Teflon cell scraper) into lysis buffer, 1.5 ml/flask (0.5% TritonX-100, 2.01% SDS at deoxycholate) from cell lysates and conditioned media.

Mammastatin proteins were immunoprecipitated by adding 5 µg 7G6 anti-Mammastatin antibody per 500 µl of 5× concentrated media or cell lysate and incubating at room temperature for 1.5 hours. Goat anti-mouse IgM second antibody (5 µg/0.5 ml) was added and the mixture incubated an additional hour. Protein G PLUS/A agarose® slurry (Oncogene Science) was added and the mixture incubated 1.5 hours at room temperature to immobilize antibody complexes.

The complexes were washed 6× with lysis buffer, each wash followed by centrifugation at 3000 ×g. SDS-PAGE loading buffer (50 µl) was added before the sample was heated to 100° C. for 3 minutes. Supernatants were resolved by SDS-PAGE, transferred to nitrocellulose, and exposed to Kodak X-AR film.

Phosphate labeling of NHMC proteins and subsequent immunoprecipitation identified 49 and 53 kD phosphoproteins in NHMC. The 49 and 53 kD phosphoproteins were not recognized in carcinoma cell lines. Carcinoma cell lines MCF-7, T47D, ZR-75-1 and MDA-MB-435 expressed a 44 kD immunoreactive protein, but this protein did not label with $^{32}$P-orthophosphate.

This study indicates more incorporated phosphate with increasing molecular weight of Mammastatin. Lack of phosphorylation of Mammastatin in transformed cell lines correlates with lack of higher molecular weight forms of the protein and lack of Mammastatin inhibitory activity.

EXAMPLE 14

Mammastatin Kinase & Phosphatase

Flasks of normal or carcinoma cells were grown to 75% confluence. Cell cultures were washed three times with TBS and then scraped into TBS with a Teflon scraper. Cell suspensions were pelleted at 1000 g by centrifugation and then resuspended in a small volume of TBS. An aliquot of each type of cell was removed for protein quantitation. Protein concentrations were then equalized at 2 mg/ml in lysis buffer (TBS with 0.5% Triton X-100 and 5 µg/ml each of aprotinin, leupeptin, and PMSF). Equal masses of normal and tumor cell proteins were mixed and incubated at 37° C. for three hours. Parallel mixtures of normal and carcinoma cell lysates were performed in the presence of 10 nM Orthovanedate (NaVO$_4$), a phosphatase inhibitor. The mixture was then separated by SDS/PAGE and analyzed by Western Blot using the 7G6 antibody. The data are shown in FIG. 8.

| | |
|---|---|
| LANE A | ZR-75-1 Lysate (30 µg) |
| LANE B | NHMC Lysate (30 µg) |
| LANE C | NHMC (30 µg) + ZR 75 (30 µg) + 10 mM NaVO$_4$ |
| LANE D | NHMC (30 µg) + ZR 75 (30 µg) |

Figure 8:
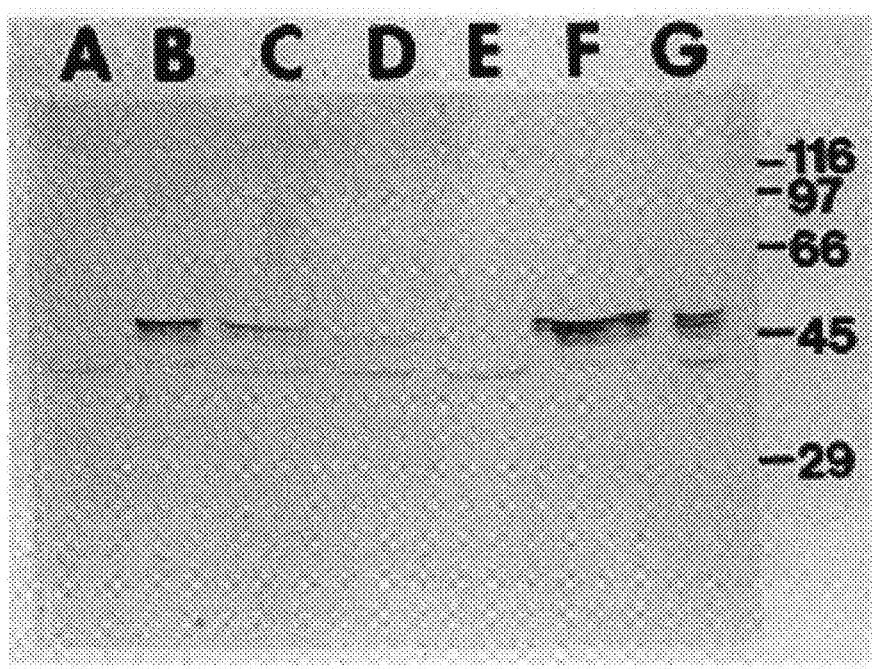
FIG. 8 is a Western Blot showing Mammastatin from normal and cancerous human mammary cells, as well as in mixed cultures of normal and cancerous cells.

As shown in FIG. 8, cancer cells (ZR-75-1)(lane A) did not produce 53/49 kD Mammastatin, as compared with NHMC (lane B). Mixing of normal and cancer cell proteins, in the presence of proteinases, reduces the amount of active, 53 kD inhibitor (lane D). However, in the presence of the tyrosine-phosphatase inhibitor NaVO$_4$, the 53 kD species is retained in the mix (lane C). These results indicate that carcinoma cells express phosphatase activity capable of eliminating phosphorylated forms of Mammastatin.

Expression of Mammastatin in normal and transformed cell lines can be measured quantitatively by Western blot analysis. Using anti-Mammastatin monoclonal antibodies, it has been demonstrated that there is a consistent difference in expression of this protein between mammary carcinoma cells and cells derived from normal mammary epithelium. Mammastatin was recognized in normal human female mammary tissue as 44, 49, and 53 kD species by Western blot analysis with anti-Mammastatin monoclonal antibody 7G6. In mammary carcinoma cells, there was inconsistent recognition of a 44 kD species, but never 49 or 53 kD immunoreactive forms. When the 49 and 53 kD forms are identified in normal cells they are phosphorylated. The 44 kD species is not phosphorylated. It is therefore possible to use immunoblot analysis to determine if Mammastatin is phosphorylated by observing the expression of the 44 and 49, and 53 kD species of Mammastatin.

EXAMPLE 15

Identification of Mammastatin in Human Sera

An enzyme-linked immunosorbant assay (ELISA) was established to detect Mammastatin, using the purified anti-Mammastatin monoclonal antibodies 6B8 and 3C6.

The antibody 6B8 was used to coat Immulon 1 96-well microtiter plates (Immulon Corp.) at a concentration of 10 µg/ml or 100 µl/well, for three (3) hours at room temperature, or overnight at 4° C. Plates were blocked with 2% BSA (Sigma) in TBS (150 mM NaCl, 100 mM Tris pH 7.4) for 30 minutes and were then incubated with either purified Mammastatin or sample sera diluted 50% in 2% BSA solution for 1.5 hours at 37° C. Microtiter plates were washed for 5 minutes, three times with 300 µl/well of TBS plus 0.1% Triton X-100 before addition of second antibody.

Second antibody was biotinylated 3C6. Antibody was biotinylated by incubation with biotin, N-hydroxy succinimate ester (Sigma) in 0.1 MNaHCO$_3$ for two hours at room temperature and 16 hours at 4° C. Antibody was dialyzed into 1 M NaCl, 50 mM Tris pH 7.4, 0.02% Azide (NaN$_3$, Sigma) before use or storage.

Biotinylated anti-Mammastatin antibody was added at 1 µg/ml and 100 µl/well, in a 2% BSAITBS solution and incubated for 1.5 hours at 37° C. Microtiter plates were washed 5 times for 5 minutes with TB S plus 0. 1% Triton X-100 as described above. Second antibody was identified with alkaline phosphatase conjugated streptavidin (Southern Biotechnology) and incubated for one hour at a dilution of 1/1000 in 2% BSA/TBS, 100 µl/well for all samples.

ELISA assays were developed colorometrically with PNPP (para-nitrophenyl phosphate Sigma), 1 mg/ml in alkaline phosphatase buffer (10 mM diethanolamine pH 9.5 (Sigma), 0.50 mM MgCl$_2$ (Sigma)). Microtitre plates were read on an ELISA reader at 405 nm at fifteen minute and thirty minute intervals.

Figure 9:
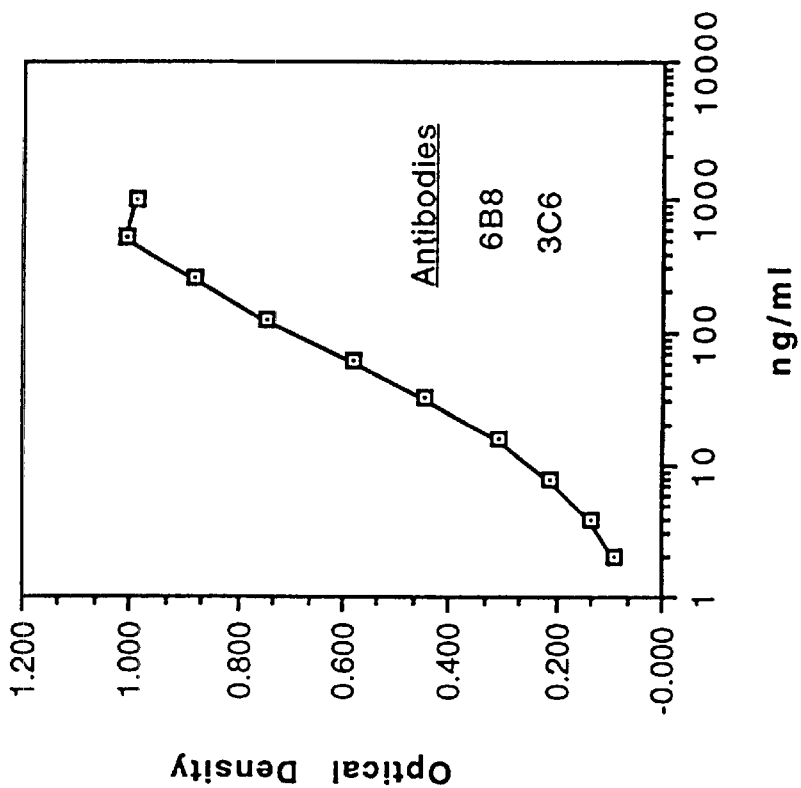
FIG. 9 is a graph showing a Mammastatin ELISA standard curve.
Figure 10:
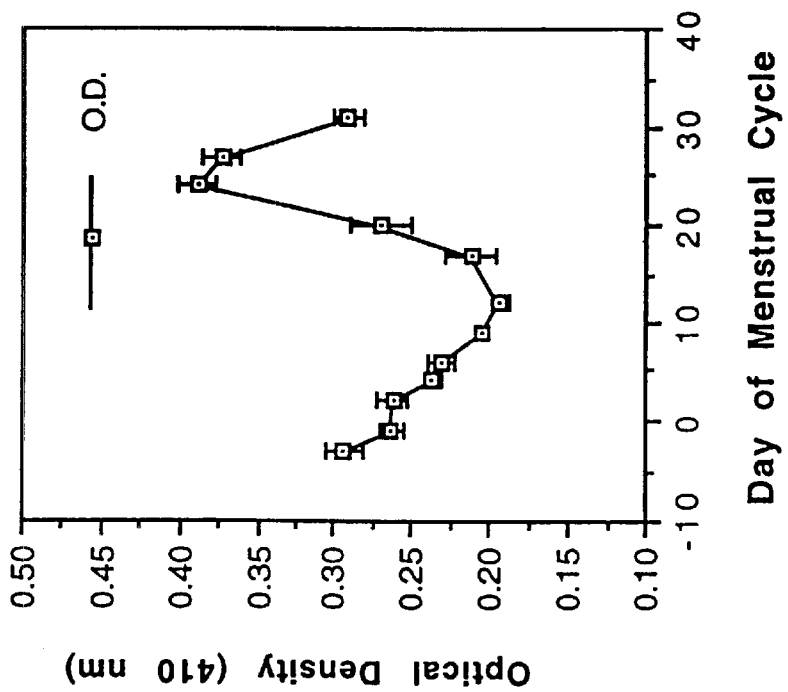
FIG. 10 is a graph showing Mammastatin in normal human serum as analyzed by ELISA.

Using chromatographically purified Mammastatin isolated from cell lysates or conditioned media, a standard curve was established for the ELISA indicating sensitivity of the assay for Mammastatin in the low nanogram range. (See FIG. 9). Quantitation of Mammastatin levels in normal human volunteer sera was performed in serum samples collected at two day intervals for one month, from a volunteer. Mammastatin levels in normal human female sera were detectable by this assay and varied between about 10 and 50 ng/ml (FIG. 10).

Figure 11:
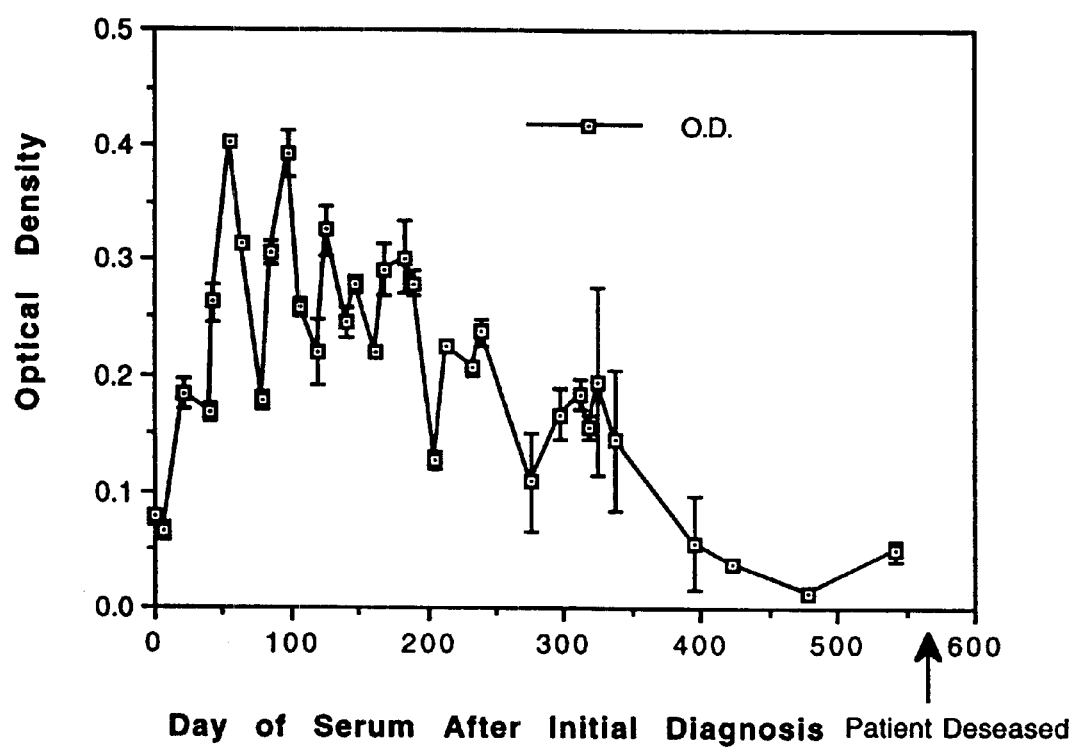
FIG. 11 is a graph showing Mammastatin levels in breast cancer patients over the course of treatment.

Mammastatin levels were also measured in sera collected from breast cancer patients. Patients diagnosed at the University of Michigan Breast Care Center with node negative breast cancer were tested for Mammastatin expression in sera throughout the course of their treatment. The data are shown in FIG. 11 and summarized below. Serum samples were collected from breast cancer patients during the entire course of their treatment on a hormonal cycling, combined modality protocol with Cytoxin, Adriamycin, Methotrexate, and 5Fu. Serum was separated from whole blood, after clotting, by centrifugation and stored at −20° C. until use. ELISA assay using 150 µl serum at 50% in 0.5% NFDM in duplicate were performed, using the 6B8 and 3C6 anti-Mammastatin antibodies in an enzyme linked—"sandwich" assay. The standard curve was generated with chromatographically purified Mammastatin and was comparable to that shown in FIG. 9.

Expression of Mammastatin varied among patients and fluctuated during the course of their treatment. It was consistently observed that Mammastatin levels became undetectable with progression to metastatic disease.

Patients diagnosed with breast cancer had low levels of Mammastatin in serum at the time of diagnosis as compared with levels in normal patient serum. Mammastatin levels generally rose on the hormonal cycling, adjuvant chemotherapy protocol. Levels of Mammastatin fluctuated on this protocol. Mammastatin levels were undetectable in patients with advanced disease, before death. The patient data sorted into four groups, as shown in the table below.

I. Group of patients whose serum Mammastatin levels continued to raise during therapy.

II. Group of patients whose serum Mammastatin levels increased initially during therapy, but then became undetectable.

III. Group of patients whose serum Mammastatin levels rose during therapy, but then fluctuated widely.

IV. Group of patients who had low serum Mammastatin levels which became undetectable with therapy.

| Summary of Mammastatin Levels in Patient Sera | | | |
|---|---|---|---|
| Group | Number | Days Followed | Outcome |
| I. | 4 p | 280 +/− 100 | Remission |
| II. | 14 p | 500 +/− 220 | Deceased |
| III. | 10 p | 380 +/− 280 | Variable |
| IV. | 5 p | 290 +/− 150 | Deceased |

EXAMPLE 16

In Vivo Efficacy of Mammastatin

CD-1 Nu/Nu homozygate, female, six week old mice (Charles River) were supplemented with Estrogen via slow release pellets, 0.72 mg/pellet, 60 day release of 17-beta estradiol (Innovative Research #SE-121). Estrogen supplemented mice were injected with $3\times10^6$ MCF-7 cells 100 µl per injection in 60% matrigel. Two injections were administered, one per flank. After seven days of tumor cell growth, Mammastatin was administered. Test mice received 1, 2, or 5 µg of Mammastatin in production media at 2 day intervals for a period of six weeks. Control mice were injected with BSA, or were not injected with tumor, but with the inhibitor alone.

Figure 13B:
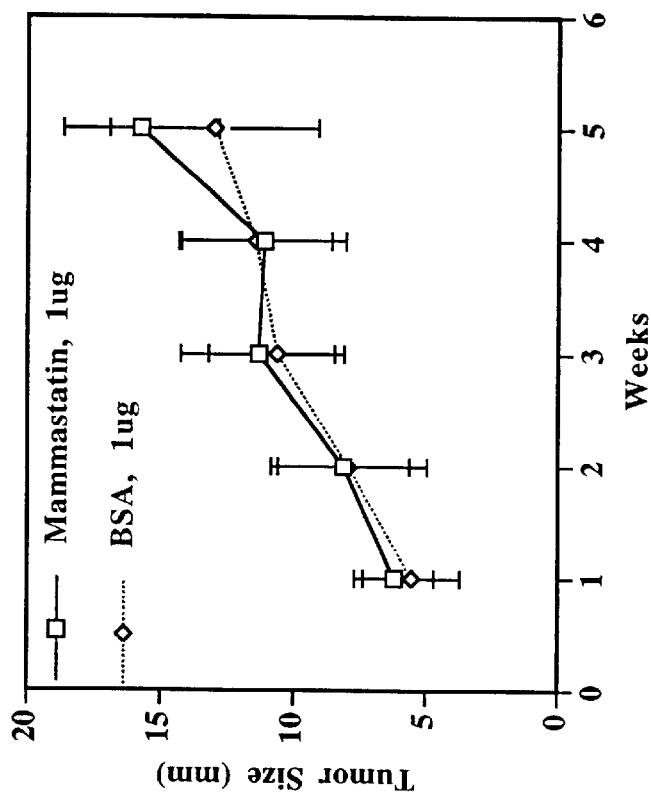
FIGS. 13A, 13B and 13C are graphs showing the effect of Mammastatin treatment on MCF7 tumor cells in nude mice.
Figure 13A:
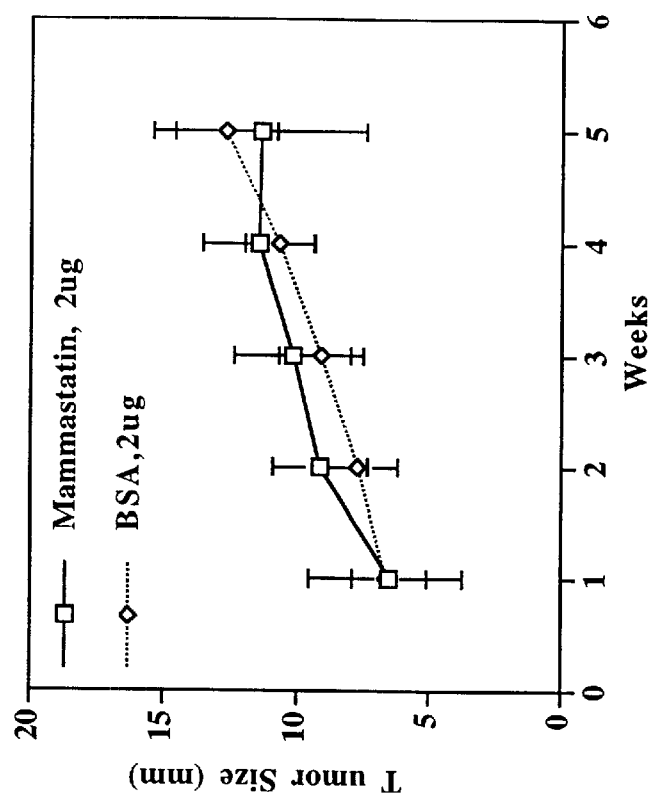
Figure 13C:
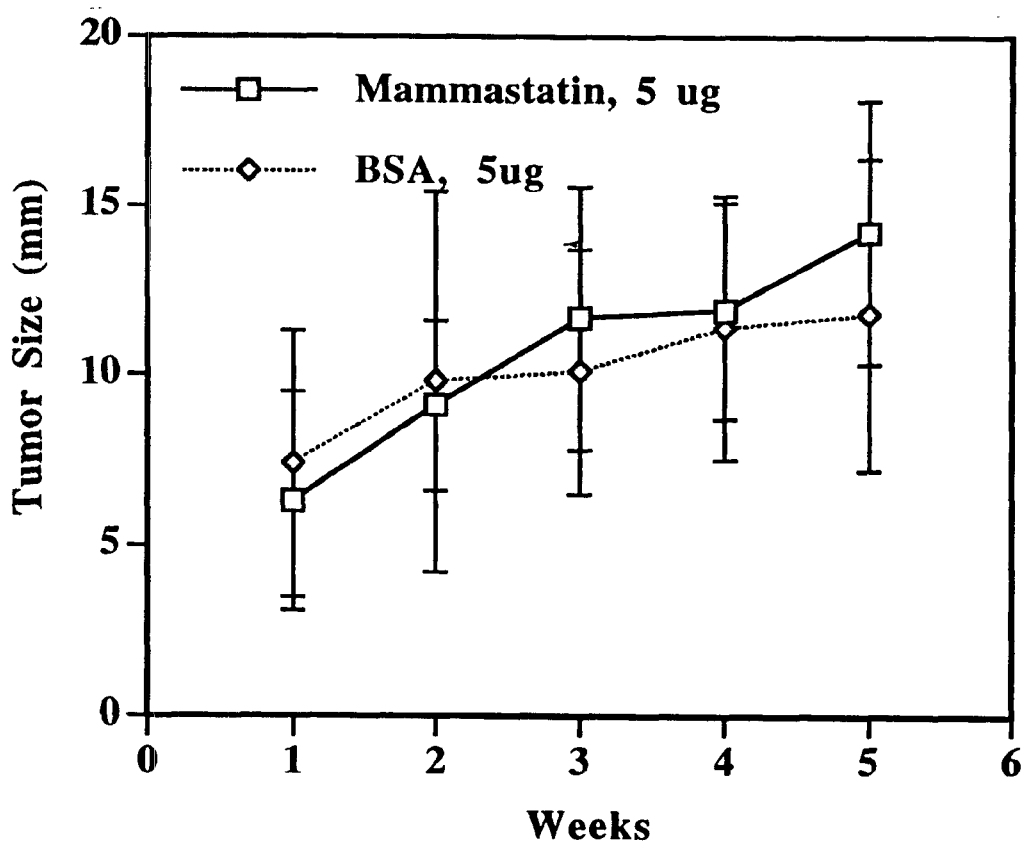

Tumor size was measured at the point of greatest diameter at weekly intervals and averaged for treatment group. The results are shown in FIGS. 13A–13C, with tumor size plotted as the mean diameter±standard deviation.

This animal study was repeated using MDA-231 tumor cells. Cells were injected at a concentration of $2\times10^6$ cells per injection as described above for MCF-7 cells.

Figure 14B:
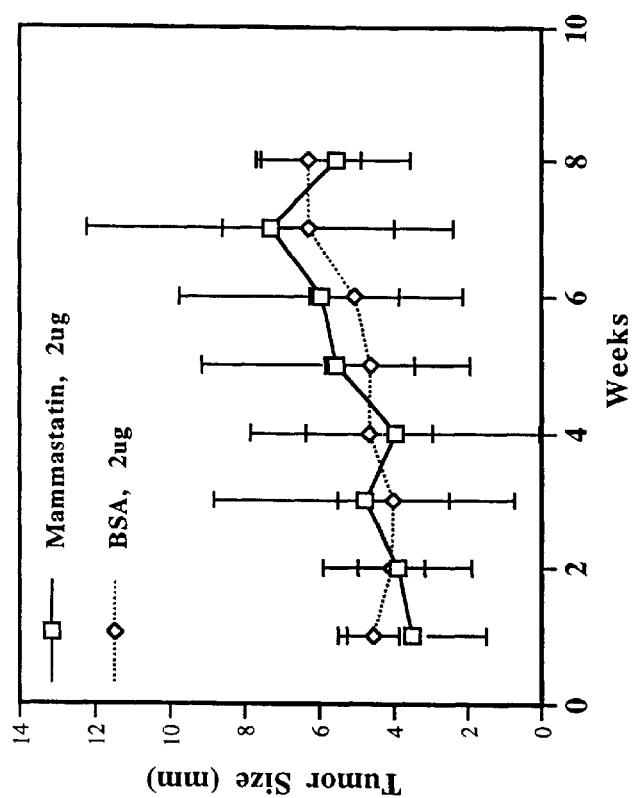
FIGS. 14A, 14B and 14C are graphs showing the effect of Mammastatin treatment on human breast tumor cells in nude mice.
Figure 14A:
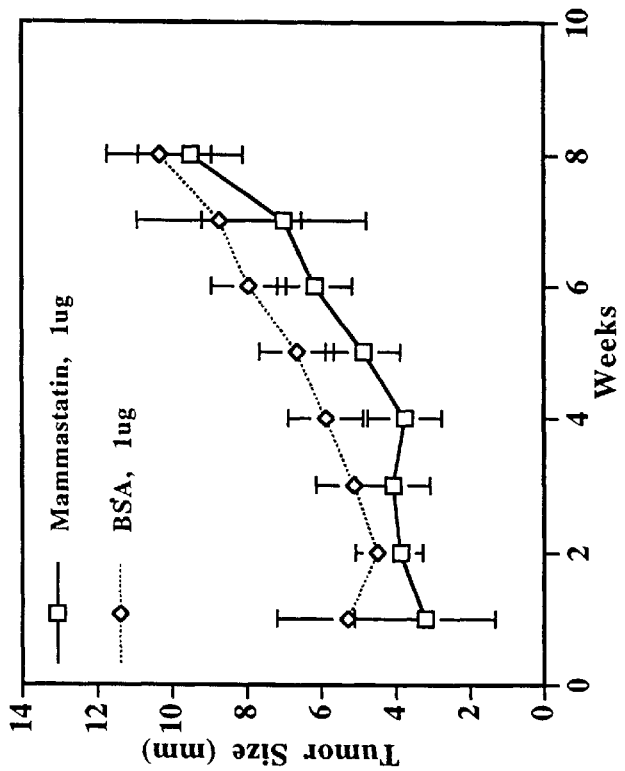
Figure 14C:
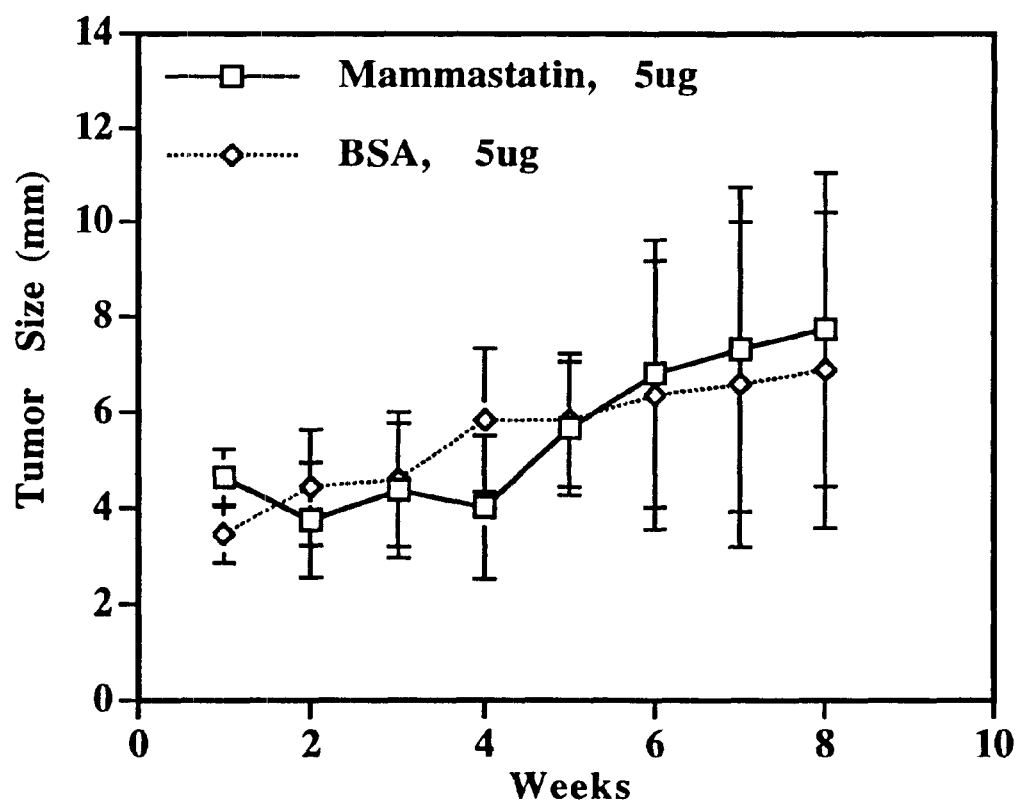

The results are shown in FIGS. 14A–14C.

The results shown were not as great as expected. The animals were injected by tail vein, resulting in less than the needed blood dose. Subsequent studies using intraperitoneal injection have resulted in more effective treatment. At doses of 5 ug/mouse and higher, tumor growth is abrogated.

EXAMPLE 17

Retrovirus Expression of Mammastatin

The Mammastatin cDNA (2.4 kilobase (kb) insert) was subcloned into a retroviral expression vector. The vector was used to transfect 3T3 fibroblast cells. Transfected cells were harvested, lysed, and the cell lysate analyzed by Western Blot.

Figure 12:
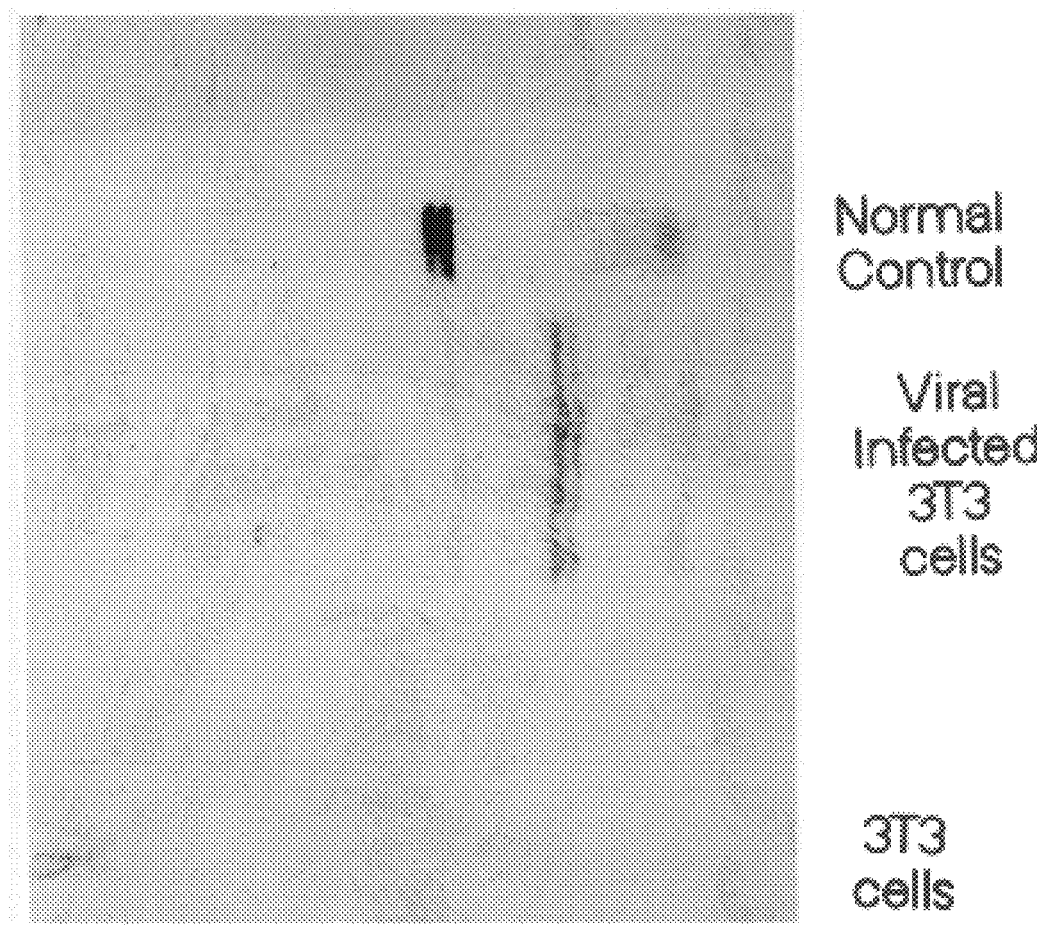
FIG. 12 is a Western blot showing expression of Mammastatin induced by retrovirus.

As shown in FIG. 12, 3T3 cells transfected with the Mammastatin-carrying retrovirus, expressed phosphorylated Mammastatin.

The above specification, examples and data provide a complete description of the manufacture and use of the composition of the invention. Since many embodiments of the invention can be made without departing from the spirit and scope of the invention, the invention resides in the claims hereinafter appended.

EXAMPLE 18

Expression of Mammastatin in Baculovirus and Cos 7 Cells

Figure 16:
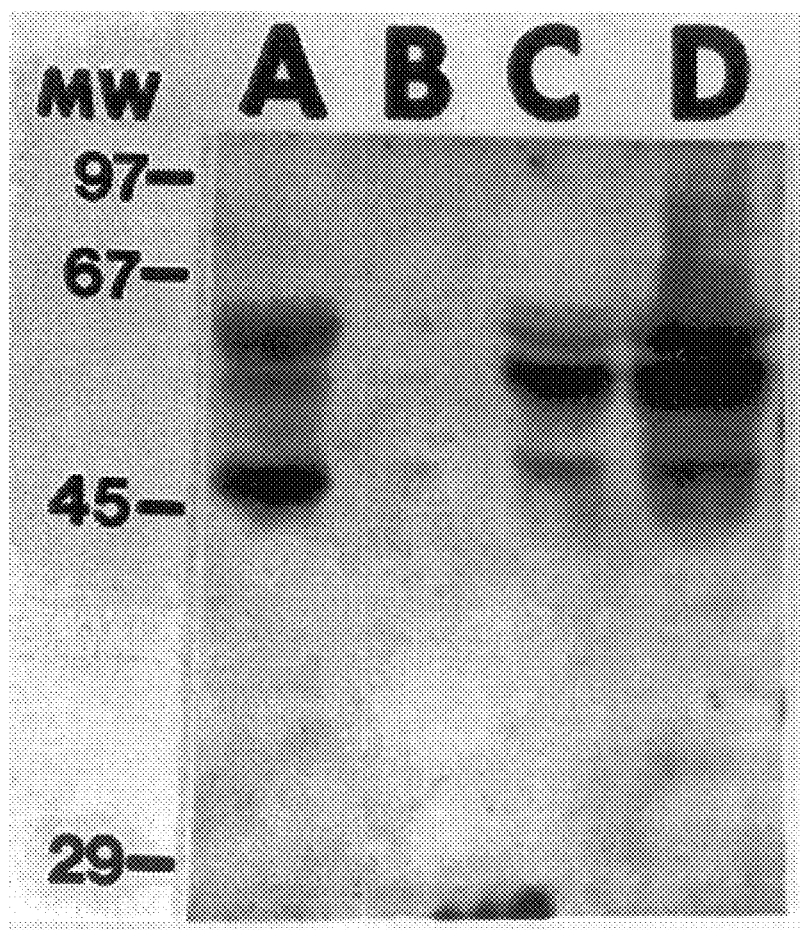
FIG. 16 is a Western blot showing recombinant Mammastatin expression in Cos-7 cells.

FIG. 16 shows the production of recombinant Mammastatin in Cos-7 Monkey Kidney Cells. Cell lysates were probed with the 7G6, anti-mammastatin monoclonal antibody. Lane A of FIG. 16 is 25 µg NHMC-20, normal human mammary cell lysate (positive control); lane B is 25 µg Cos-7 cell lysates, transfected with pcDNA3 (negative control); lane C is 10 µg Cos-pMammB cell lysate, transfected with pcDNA3/mammastatin construct; and lane D is 20 µg Cos-pMammB cell lysate. Experiment was repeated 3 times with similar results.

Induction of recombinant mammastatin expression in Cos-7 cells demonstrates that the mammastatin gene codes for authentic mammastatin. Furthermore, the observation that Cos-7 cells express the different forms of mammastatin associated with phosphorylation of the protein suggests that mammastatin will be phosphorylated and active when produced in eucaryotic cell lines other than human mammary cells. Stable transfectants have been selected to allow perpetual synthesis of recombinant mammastatin.

EXAMPLE 19

Production of Mammastatin by Normal Human Breast Epithelial Cells in Culture

Healthy breast tissue was obtained from reduction mammoplasty, sterile, and direct from the operating room. The tissue was minced under sterile conditions in a laminar flow hood in a solution containing 4 units per gram of type III collagenase (Life Sciences, Bethesda, Md.). The minced tissue was incubated overnight in a shaking water bath at 37° C. to allow collagenase digestion.

Collagenase digested breast tissue, a viscous fluid containing a variety of cell types and lipid released from adipose cells, was centrifuged to separate lipid, aqueous solution, and other cell types. The collagenase-digested material was spun at 1000 rpm in a table top centrifuge at room temperature for 5 minutes. Adipose cells and free lipid partitioned to the top half of the centrifuge tube, and were withdrawn by aspiration and discarded. The aqueous supernatant positioned above the cell pellet was also withdrawn by aspiration and discarded. The remaining cell pellet was washed with sterile solutions of mammalian growth media, DMEM, pH 7.4. The washing was continued until the supernatant from the washes was no longer turbid (for example about 4 washes). The washed cells were resuspended in growth media and allowed to settle by gravity for 30 minutes at 40° C. Because red blood cells are enucleated and are less dense than nucleated epithelial cells, this procedure resulted in removal of the red blood cells from the sedimented epithelial cells, by withdrawing the supernatant containing the red blood cells. This sedimentation procedure was repeated until no red color remained in the cell pellet, e.g., about 2 times. The remaining cell pellet was resuspended in a nutrient rich DMEM/F12 growth media containing 5% equine serum, 10 µg/ml epidermal growth factor, 100 ng/ml of cholera toxin, 500 ng/ml hydrocortisone, 10 µg/ml insulin, 100 units/ml penicillin and streptomycin, and 1 mM concentration of calcium chloride. Physiological concentrations of calcium helped to promote cell attachment and outgrowth in cell culture. The cell suspensions were incubated in sterile tissue culture flasks at 37° C. with a 5% $CO_2$ concentration.

Initial cultures of normal breast tissue contain a mixed cell population. The adipocytes, neurons, and vascular tissue are significantly reduced by the differential centrifugation process described above. Connective tissue cells are present in significant amounts. To remove non-epithelial cells, a differential attachment method was used. Fibroblasts, neurons, and other cell types in breast tissue all attach to tissue culture plastic more rapidly than epithelial cells. In addition, all of these cell types are removed from tissue culture plastic by trypsin more rapidly than epithelial cells. To enrich the cultures for breast epithelial cells, cultures beginning to form a monolayer (5–7 days after initial plating) are treated with a trypsin:EDTA solution (250:1) molar ratio. The majority of cells were removed within 5 minutes of incubation at 37° C. The remaining attached cells were more than 90% epithelial breast cells. These cells were saved and returned to the growth medium described above with 40 μM calcium chloride. The fibroblast cells were removed from the trypsinized culture flasks, collected by centrifugation, resuspended in growth medium, and plated onto tissue culture plastic for 30 minutes at 37° C. The attached cells were predominantly fibroblasts. The cells that did not attach were significantly enriched for fibroblast cells (50–80%). These suspended cells were removed and allowed to settle in fresh tissue culture flasks. This process was repeated twice to obtain cell populations that were predominantly epithelial. Because cholera toxin promotes epithelial cell growth and inhibits fibroblast growth, and because fibroblasts do not grow well in reduced calcium, the cultures were approximately 100% epithelial within one week in the low calcium medium described above. These cultures of normal human mammary cells (NHMC) produced Mammastatin into the culture medium.

Nutrient medium used to grow the NHMC containes 5% equine serum, which is not acceptable for human injection. The equine serum proteins must either be purified away from the mammastatin protein, or the cells grown in medium devoid of the serum. Normal cells can only be maintained in the absence of serum for about seven to ten days. In order to produce a significant quantity of serum free mammastatin over a prolonged period of time, the cells were alternately grown in serum-free and serum-containing medium.

NHMC were grown to complete confluence in growth media as described above. The cells began to bud in solution as they grew, when cells covered the available surface of the flask budding cells were collected and transferred to new flasks. Confluent flasks were rinsed three times with sterile saline, with a five minute saline incubation between washes to remove serum protein. Cells were then provided with serum free "production medium" that was essentially the growth medium devoid of serum, cholera toxin, and hydrocortisone. Cells were maintained on the production medium for about 4 days (96 hours), with collection of the medium, and a return of the cells to growth medium for at least four days. The typical batch size for mammastatin produced in this way was 1–2 liters.

Mammastatin has also been produced in a Bioreactor, the Bioflow 3000, New Brunswick Scientific. In this perfusion reactor, cells were attached on tissue culture treated fibracell disks. The cell-attached disks were maintained in a basket in the reaction vessel and perfused with media. When NHMC were introduced to the reactor, they populate the fibracell disks and were fed by the perfusion of media. Conditioned media was harvested from the reactor and refrigerated.

EXAMPLE 20

Dot Blot Serum Assay for Mammastatin

Serum from a 25 year old healthy female was obtained and compared with serum from a breast cancer patient (Stage IV), an undiagnosed sibling of the patient, and from the patient's mother, whose family has a history of breast cancer. The serum samples were compared in an immunoassay for the presence of Mammastatin. Blood samples from multiple breast cancer patients taken on day of diagnosis were also analized in the immunoassay. Normal human mammary cell (NHMC) conditioned media was used as a standard control. Standard NHMC mammastatin contained approximately 50 ng/ml as determined in a dot blot assay with mammastatin protein standard chromatographically purified.

Individual blood samples were collected into vacutainer tubes, and the serum separated from whole blood. Serum samples (250 or 500 μl volume) were applied without dilution to nitrocellulose by suction using a 96 well, S&S Dot-Blot manifold. Conditioned medium was prepared as described for Example 19. Samples on the nitrocellulose filters were washed with Triton X-100 in TBS, blocked with non-fat dry milk (5% in TBS) and incubated with 1 μg/ml of first anti-mammastatin antibody (7G6 mouse IgM) in 5% non-fat dry milk for 1.5 hours at room temperature, followed by incubation with 1 μg/ml of second antibody (goat antimouse 1 gM conjugated to alkaline phosphatase) in 5% non-fat dry milk for one hour and room temperature. The alkaline phosphatase color reaction was developed using nitroblue-tetrazolium and BCIP.

Figure 15:
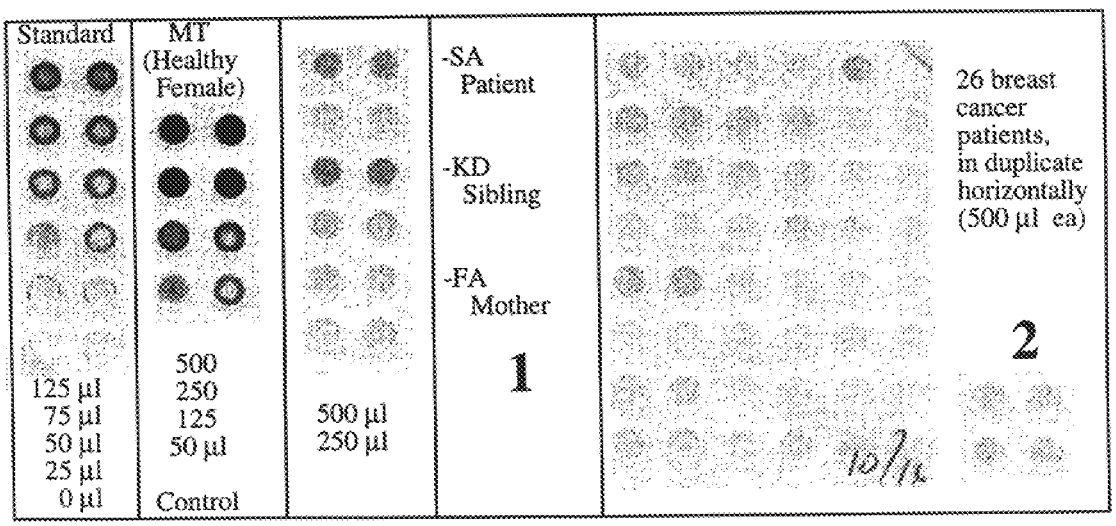
FIG. 15 is a dot blot assay showing Mammastatin in blood from normal females versus the absence of Mammastatin in blood from breast cancer patients.

As shown in FIG. 15, the amount of Mammastatin in the sample was quantitated against the standard curve obtained from normal breast cell conditioned medium. Serum obtained from healthy females contained readily detectable amounts of Mammastatin, as indicated by darkly colored blots, whereas serum from diagnosed breast cancer patients. and from undiagnosed family members showed little or no Mammastatin.

Additional samples were obtained from breast cancer patients on day of diagnosis, from healthy members of a breast cancer patient's family, and from healthy females and males. The serum was processed as described above in order to analyze Mammastatin. The dot blots were evaluated as "negative or low" or "positive or high" to indicate the intensity of the developed color reaction. Data are shown in the following table.

| Sample | Number | Negative or Low | Positive or High |
|---|---|---|---|
| Breast Cancer patient | 89 | 83 (93%) | 6 (7%) |
| Healthy female | 11 | 2 (18%) | 9 (82%) |
| Healthy member of high risk family | 4 | 4 (100%) | 0 |
| Male | 3 | 2 | 1 |

EXAMPLE 21

Treatment of Human Breast Cancer Patients

Twenty-nine (29) Sage IV breast cancer patients with recurrent breast cancer, who had failed, or were failing on chemotherapeutic regimes were given access to Mammastatin protein. The protein was produced as described above for Example 19, and provided in production medium, with the required dose in a 3 ml injection volume. Patients administered the protein intravenously according to their prescribed regimen. In general, one daily dose was injected. The selected dose was that which provided physiological amounts of Mammastatin in the patient's bloodstream, e.g., 5–50 ng/ml in healthy women. The dosage and frequency for each patient are indicated in the table below.

| Patient Number | Dose (ug) | Schedule | Result |
|---|---|---|---|
| 1. | 125 | daily | complete remission followed by relapse* |
| 2. | 125 | daily | complete remission; pain if therapy stopped |
| 3. | 75 | daily | non-responder* |
| 4. | 75 | daily | partial remission; possible immune reaction** |
| 5. | 75 | daily | non-responder* |
| 6. | 125 | daily | partial remission |
| 7. | 125 | daily | partial remission* |
| 8. | 75 | daily | non-responder* |
| 9. | 125 | every third day | complete remission |
| 10. | 125 | daily | non-responder |
| 11. | 125 | daily | partial remission |
| 12. | 125 | daily | non-responder# |
| 13. | 150 | daily | non-responder* |
| 14. | 75 | daily | non-responder# |
| 15. | 125 | daily | partial remission |
| 16. | 125 | daily | partial remission |
| 17. | 75 | daily | non-responder, infection** |
| 18. | 125 | daily | partial remission |
| 19. | 125 | daily | partial remission |
| 20. | 125 | daily | partial remission |
| 21. | 125 | every other day | non-responder**; alternative therapy |
| 22. | 125 | every other day | partial remission |
| 23. | 125 | every other day | non-responder |
| 24. | 125 | daily | non-responder |
| 25. | 125 | daily | non-responder |
| 26. | 125 | daily | partial remission |
| 27. | 125 | daily | partial remisssion |
| 28. | 125 | every other day | partial remission |
| 29. | 125 | daily | |

| Total | Responders | % Responders | % without liver involvement | % without lung or liver involvement |
|---|---|---|---|---|
| 29 | 17 | 59 | 81 | 89 |

*patient deceased
**Patient withdrawn from therapy
evidence of improvement in jaundice prior to death Of the group of 29 patients, six, having late stage liver disease, did not survive. These six patients displayed clinical evidence of liver failure before receiving Mammastatin, and were not helped by the treatments. One patient showed signs of decreased jaundice before her liver failed, but all six of these patients appeared to die of nitrogen toxicity common to patients with advanced liver cancer.

Of the remaining patients, two have died of their disease. One appeared to be disease-free after two months of Mammastatin therapy. This patient was removed from therapy, and relapsed within two months. The patient's disease was never brought back under control and she died of liver involvement. The second patient died after 4 months of treatment, having never shown any sign of response to the therapy. There was no sign of toxicity in any of these patients, although the dose of Mammastatin in these latter two patients was increased ten fold.

Of the 19 patients currently receiving Mammastatin therapy, the majority show signs of positive benefit and no signs of adverse reaction. It is unclear if three of these patients are receiving any benefit from Mammastatin. The other 16 patients show definite clinical signs of benefit including decreased tumor markers (CA15-3 and CA27-29) to normal levels, decreased size of palpable tumor masses, decreased disease as evidenced on MRI scan, and decreased pain. Several of these patients show improvement to the point of being considered disease free. However, it has consistently been observed that denying these patients protein for periods of three to five days results in resumption of disease activity as evidenced by increased pain, even in patients that show no signs of disease. Resumption of protein treatments decreases or eliminates the symptoms of increased pain within 2–4 hours.

It has also been observed that Mammastatin levels in the blood decline after long term treatment, suggesting a negative feedback system. This decline in constant blood levels is successfully avoided by providing Mammastatin daily for a period of about 28 days, followed by 2–3 days without protein.

EXAMPLE 22

Recombinant Mammastatin for Human Therapy

Recombinant Mammastatin has been produced in Cos-7 monkey kidney cells, chinese hamster ovary (CHO) cells, and Sf9 insect cells by transfecting the cells with a plasmid containing the Mammastatin cDNA sequence. The Mammastatin cDNA has been stably integrated into the genomes of these producing cell lines, and secrete protein immunoreactive with growth inhibitory activity.

To produce Mammastatin from these cells and isolate the protein for human use, the cell lines are grown in serum free medium for approximately 48 to 72 hours. The media is withdrawn and protein purified from conditioned medium, either by ion exchange chromatography in Tris buffer, pH7.5, using a sodium chloride gradient from about 0.1 M to about 0.5 M, collecting the Mammastatin fraction at about 0.2 M. The protein fraction is then dialized against normal saline, diluted if necessary, and filter sterilized.

In an alternative method, Mammastatin is produced as a fusion protein in Cos7 or SF9 cells. The fusion protein contains a histidine tag (six histidine residues) and a Factor X proteinase cleavage site. The Mammastatin expressing cells are cultured, preferably in 1% serum-containing media, the conditioned media is collected and passed over a nickel chelating resin. The His-fusion protein adheres to the column, is washed with 50 mM TRIS, pH 7.5, 0.1 M NaCl, and is slowly eluted with TRIS-NaCl containing 10 Unit/ml Factorxproteinase. This liberates Mammastatin from the His fusion. Mammastatin is separated by molecular sieve chromatography, or by ion exchange chromatography as described above.

TABLE 1

MAMMASTATIN DNA SEQUENCE

TGGGGCTCCACCCCGGTGGCGGCCGCTCTAGAACTAGTGGATCCCCCGGGCTGCAGGAATTCGGCACGAGCACGGTGA

AGAGACATGAGAGGTGTAGAATCCGTGGGAGGCCCCCGGCGCCCCCCGGTGTCCCCGCGAGGGGCCCGGGGCGGGGT

CCGCCGGCCCTGCGGGCCGCCGGTGAAATACCACTACTCTTATCGTTTTTTCACTGACCCGGTCGAGCG\GGGGGCGA

TABLE 1-continued
MAMMASTATIN DNA SEQUENCE

```
GCCCCGAGGGGCTCTCGCTTCTGGCGCCAAGCGCCCGGCCGCGCGCCGGCCGGGCGCGACCCGCTCCGGGGACAGTGC
CAGGTGGGGAGTTTGACTGGGGCGGTACACCTGTCAAACGGTAACGCAGGTGTCCTAAGGCGAGCTCAGGGAGGACAG
AAACCTCCCGTGGAGCAGAAGGGCAAAAGCTCGCTTGATCTTGATTTTCAGTACGAATACAGACCGTGTAAGCGGGGC
CTCACGATCCTTCTGACCTTTTGGGTTTTAAGCAGGAGGTGTCAGAAAAGTTACCACAGGGATAACTGGCTTGTGGCG
GCCAAGCGTTCATTAGGACGTCGCTTTTTGATCCTTCGATGTCGGCTCTTCCTATCATTGTGTAGCAGAATTCACCAA
GCGTTGGATTGTTCACCCACTAATAGGGAACGTGAGCTGGGTTTAGACCGTCGTGAGACAGGTTATTTTTACCCTACT
GATGATGTGTTGTTGCCATGGTTATCCTGCTCAGTACGAGAGGAACCGCAGGTTCAGACATTTGGTGTATGTGCTTGG
CTGAGGAGCCAATGGGCGAAGCTACCATCTGTGGGATTATGACTGACGCTCTAAGTCATGAATCCCGCCCAGGCGGA
ACGATACGGCAGCGCCGCGGAGCCTCGGTTGGCCTCGGATTAGCCGGTCCCCGCCTGTCCCGCCGGCGGGCCGCCC
CCCCCCCTCCACGCGCCCCGCGCGCGGGAGGGCGCGTGCCCCGCCGCGCGCCGGGACCGGGGTCCGGTGCGGAGTG
CCCTTCGTCCTGGGAAACGGGGCGCGGCCGGAAAGGCGGCCGCCCCCTCGCCCGTCACGCACCGCACGTTCGTGCTCG
TGCCGAATTCGGCACGAGTGCACCCATTCACAATATACATACAAGTGCATGTATCTTTATGATATAATGAATTCTTTT
CCTTTGGGTAGATATCCAGTAGTGGGATTGCTAGATCACCTGGTAGTTCTATTTCTGGTTTATTTAGAAATCTTCATA
CTGATTTCCATAGAGGTTGTACAAATTTACATCCCTACCAAAGTGATTTTTTAAATATGAAAGAATGGTCTGGAGAA
ATGCCCCTCATTAGTATCCCCCTTTTACCTCTCTACTGCAGAATGACTTCAAGGGGTACAGGTATTTACAAGTTTCAT
TATACAGACAAATTGAATATTGAAATTTTCTGCATAAGAGGCACAGATTTTAGGATTCAAAGTTGTATGAACAAGGAC
AAGTGCTCTAGGGACTTGCAAAGCTGGAATTGGAAATCTCAGATGAAATACATTTCTAGTAGTACCACCAGCATATAT
TCTACTGAATTGGCTTTTGTGATCATCATTAATACCTACTTATTAAAACTAATGAAAAGGGTTTATATCAAATATACT
TTAAGGTATAAAAATCAAATTATAGGTAAAGCTGTTTTCTTTAGCATTTTAATTTCAAAACATAAAATAGCTACCGTC
TATTGGGCATTTATACTGTACCAGACACTGTGTTTGTCACATTTCAAAAATGTTCTCATGGTAATGTTCACAATAATT
CTGTCGGGTGAGAAAATAGTCTTACCGTAGTAAGACTATTCAGTAAAACGAAACCTCTGAACCTTGGAGTTCAACTTG
CGCAAAGTTAGTAACAGGACTAGGACTTGAACCTGAACCATCACACTCCAGATCTCTCCATACCACACTGCTAGCACA
TGTGCCTGTCATCTTATTCCTGGCTCCCTTTTTTATTTCCTTTCCCTTCCTCCCACAACCCCTTTTTCCCCCCATTTC
TTTCTTTCTTTTTATTTGTTAATTACATAACTAATACATGTTTATCAGAACAATTGATATAGCACAAAAGGATATAAA
GTACGGGGAGTGATAGCTCATCCCTGTAATCCTAGCACTTTGGAAGGCCAAGGCAGGCAGATCACTTTGAGTCCAGA
GTTCGAGACCAGCCTGGGCAACATGGTG:AAACCCTGTCTCTACAAAAAAATACAAAAAATTTAGCCGGGCGTGCTGG
CACACACCTGTAGTCTCAGCTACTCTGAGGGCTGAGGTGGGAAGATTGATTGAGCCCAGGAGGTGGAAGCTGCAGCAG
TGCGCTGAGATTGCGCCATTGCACTCCAGCCTGGGTGAGAGAGAGAGACCCTGTCTCCAAAAAAAAAAAAAAAAAAAA
A
```

*start codon ATG at nucleotide 86
stop codon TA6 at 2091

---

I claim:

1. A method for treating breast cancer comprising:

administering to a patient a therpeutically effective dose of a protein expressed from a 2.4 kilobase BamHl-Xhol nucleic acid inser of deposited clone ATCC No. 97451.

2. The method of claim 1, wherein said administering is repeated to maintain a therapeutically effective amount of the protein in the patient's blood.

3. The method of claim 1, wherein said protein is administered daily for approximately 25 to 28 days, followed by no administration of said protein for 5 days or less.

4. The method of claim 3, wherein said protein is administered daily for approximately 25 to 28 days followed by no administration of said protein for about 2 to 3 days.

5. The method of claim 1, wherein said dose is approximately 75 µg/day to about 150 µg/day.

6. The method of claim 5, wherein said dose is approximately 125 µg/day.

7. The method of claim 1, wherein said dose is approximately 125 µg administered every other day or approximately 125 µg administered every third day.

8. A method from treating breast cancer comprising:
administering to a patient a protein expressed from a 2.4 kilobase BamHI-XhoI nucleic acid insert of deposited clone ATCC No. 97451, in an amount to provide a therapeutic blood concentration of the protein.

9. The method of claim 8, wherein said protein is administered daily for approximately 25 to 28 days, followed by no administration of said protein for 5 days or less.

10. The method of claim 9, wherein said protein is administered daily for approximately 25 to 28 days followed by no administration of said protein for about 2 to 3 days.

11. The method of claim 8, wherein said therapeutic blood concentration is about 50 ng/ml to about 75 ng/ml.

12. The method of claim 8, wherein said administering provides a therapeutic blood concentration from about 5 ng/ml to about 50 ng/ml.

13. The method of claim 8, wherein said administering is by injection, infusion, or slow-release depot.

14. The method of claim 8, wherein said administering comprises administering said protein once a day.

15. The method of claim 8, wherein said administering comprises administering said protein once every two days.

16. The method of claim 8, wherein said administering comprises administering said protein by continuous infusion.

17. The method of claim 1, wherein said administering is by injection, infusion, or slow-release depot.

18. The method of claim 1, wherein said administering comprises administering said protein by continuous infusion.

* * * * *

UNITED STATES PATENT AND TRADEMARK OFFICE
CERTIFICATE OF CORRECTION

PATENT NO.     : 6,451,765 B1
DATED          : September 17, 2002
INVENTOR(S)    : Paul R. Ervin, Jr.

It is certified that error appears in the above-identified patent and that said Letters Patent is hereby corrected as shown below:

Title page,
Item [56], OTHER PUBLICATIONS,
"Inhibitingy" should be -- Inhibiting --
"McMabon" should be -- McMahon --
"an M, 13,000 Polypeptide" should be -- an $M_r$ 13,000 Polypeptide --
Insert -- FOREIGN PATENT DOCUMENTS
WO 89/11491A 11/30/1989
WO 89/11492A 11/30/1989 --

Column 3,
Line 27, "Marunastatin" should be -- Mammastatin --

Column 4,
Line 9, "Marnmastatin" should be -- Mammastatin --

Column 10,
Line 21, "epitheliurn" should be -- epithelium --

Column 33,
Line 64, "inser" should be -- insert --

Signed and Sealed this

First Day of July, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 2418
<212> TYPE: DNA
<213> ORGANISM: Homo sapiens

<400> SEQUENCE: 1

-continued

```
tggggctcca ccccggtggc ggccgctcta gaactagtgg atcccccggg ctgcaggaat    60
tcggcacgag cacggtgaag agacatgaga ggtgtagaat ccgtgggagg ccccggcgc    120 cccccggtg tcccgcgag gggcccgggg cggggtccgc cggccctgcg ggccgccggt    180
gaaataccac tactcttatc gttttttcac tgacccggtc gagcggggg gcgagccccg    240 aggggctctc gcttctggcg ccaagcgccc ggccgcgcgc cggccgggcg cgacccgctc    300
cggggacagt gccaggtggg gagtttgact ggggcggtac acctgtcaaa cggtaacgca    360
ggtgtcctaa ggcgagctca gggaggacag aaacctcccg tggagcagaa gggcaaaagc    420
tcgcttgatc ttgattttca gtacgaatac agaccgtgta agcggggcct cacgatcctt    480 ctgaccttt gggttttaag caggaggtgt cagaaaagtt accacaggga taactggctt    540
gtggcggcca agcgttcatt aggacgtcgc ttttgatcc ttcgatgtcg gctcttccta    600
tcattgtgta gcagaattca ccaagcgttg gattgttcac ccactaatag gaacgtgag    660 ctgggtttag accgtcgtga gacaggttat ttttacccta ctgatgattg tttgttgcca    720
tggttatcct gctcagtacg agaggaaccg caggttcaga catttggtgt atgtgcttgg    780
ctgaggagcc aatggggcga agctaccatc tgtgggatta tgactgacgc tctaagtcat    840
gaatcccgcc caggcggaac gatacggcag cgccgcggag cctcggttgg cctcggatta    900
gccggtcccc cgcctgtccc cgccggcggg ccgccccccc cctccacgc gccccgcgcg    960 cgcgggaggg cgcgtgcccc gccgcgcgcc gggaccgggg tccggtgcgg agtgcccttc    1020
gtcctgggaa acggggcgcg gccggaaagg cggccgcccc ctcgcccgtc acgcaccgca    1080
cgttcgtgct cgtgccgaat tcggcacgag tgcacccatt cacaatatac atacaagtgc    1140
atgtatcttt atgatataat gaattctttt cctttgggta gatatccagt agtgggattg    1200
ctagatcacc tggtagttct atttctggtt tatttagaaa tcttcatact gatttccata    1260
gaggttgtac aaatttacat ccctaccaaa gtgatttttt taaatatgaa agaatggtct    1320
ggagaaatgc ccctcattag tatcccccctt ttacctctct actgcagaat gacttcaagg    1380
ggtacaggta tttacaagtt tcattataca gacaaattga atattgaaat tttctgcata    1440
agaggcacag atttttaggat tcaaagttgt atgaacaagg acaagtgctc tagggacttg    1500
caaagctgga attggaaatc tcagatgaaa tacatttcta gtagtaccac cagcatatat    1560
tctactgaat tggcttttgt gatcatcatt aatacctact tattaaaact aatgaaaagg    1620
gtttatatca aatatacttt aaggtataaa atcaaatta taggtaaagc tgttttctttt    1680 agcattttaa tttcaaaaca taaaatagct accgtctatt gggcatttat actgtacgag    1740
acactgtgtt tgtcacattt caaaaatgtt ctcatggtaa tgttcacaat aattctgtcg    1800
ggtgagaaaa tagtcttacc gtagtaagac tattcagtaa aacgaaacct ctgaaccttg    1860
gagttcaact tgcgcaaagt tagtaacagg actaggactt gaacctgaac catcacactc    1920
gagatctctc cataccacac tgctagcaca tgtgcctgtc atcttattcc tggctccctt    1980 tttatttcc tttcccttcc tcccacaacc ccttttttccc cccatttctt tctttctttt    2040
tatttgttaa ttacataact aatacatgtt tatgagaaca attgatatag cacaaaagga    2100
tataaagtac gggggagtga tagctcatcc ctgtaatcct agcactttgg aaggccaagg    2160
caggcagatc actttgagtc cagagttcga gaccagcctg gcaacatgg tgaaaccctg    2220 tctctacaaa aaatacaaa aaatttagcc gggcgtgctg gcacagacct gtagtctcag    2280
ctactctgag ggctgaggtg ggaagattga ttgagcccag gaggtggaag ctgcagcagt    2340
```

-continued

```
gcgctgagat tgcgccattg cactccagcc tgggtgagag agagagaccc tgtctccaaa    2400
aaaaaaaaaa aaaaaaaa                                                  2418
```

<210> SEQ ID NO 2
<211> LENGTH: 9
<212> TYPE: PRT
<213> ORGANISM: Homo sapiens

<400> SEQUENCE: 2

Gly Gln Leu Glu Tyr Gln Asp Leu Arg
 1               5

<210> SEQ ID NO 3
<211> LENGTH: 13
<212> TYPE: PRT
<213> ORGANISM: Homo sapiens

<400> SEQUENCE: 3

Tyr Glu Arg Asp Leu Lys Gly Arg Asp Pro Val Ala Ala
 1               5                  10

<210> SEQ ID NO 4
<211> LENGTH: 27
<212> TYPE: DNA
<213> ORGANISM: Homo sapiens

<400> SEQUENCE: 4

```
tgggatccct tcgccacgag cacggtg                                          27
```

<210> SEQ ID NO 5
<211> LENGTH: 24
<212> TYPE: DNA
<213> ORGANISM: Homo sapiens

<400> SEQUENCE: 5

```
tgggatcctt cgccacgagc acgg                                             24
```

<210> SEQ ID NO 6
<211> LENGTH: 24
<212> TYPE: DNA
<213> ORGANISM: Homo sapiens

<400> SEQUENCE: 6

```
tgggatcctt cgccacgagc acgg                                             24
```

<210> SEQ ID NO 7
<211> LENGTH: 24
<212> TYPE: DNA
<213> ORGANISM: Homo sapiens

<400> SEQUENCE: 7

```
tttttttttt ttgggccctt aagt                                             24
```